United States Patent [19]

Danishefsky et al.

[11] Patent Number: 5,446,047

[45] Date of Patent: Aug. 29, 1995

[54] CAMPTOTHECIN ANALOGUES

[75] Inventors: Samuel J. Danishefsky, New Haven, Conn.; William G. Bornmann; Wang Shen, both of New York, N.Y.

[73] Assignee: Sloan-Kettering Institute for Cancer Research, New York, N.Y.

[21] Appl. No.: 919,188

[22] Filed: Jul. 23, 1992

[51] Int. Cl.[6] ............... A61K 31/435; C07D 491/22
[52] U.S. Cl. ..................... 514/280; 546/48
[58] Field of Search ................ 546/48; 514/280

[56] References Cited

U.S. PATENT DOCUMENTS

| | | | |
|---|---|---|---|
| 3,894,029 | 7/1975 | Winterfeldt et al. | 546/48 |
| 4,031,098 | 6/1977 | Sugasawa | 546/48 |
| 4,399,282 | 8/1983 | Miyasaka et al. | 546/48 |
| 4,473,692 | 9/1984 | Miyasaka et al. | 546/48 |
| 4,513,138 | 4/1985 | Miyasaka | 546/48 |
| 4,545,880 | 10/1985 | Miyasaka | 546/48 |
| 4,604,463 | 8/1986 | Miyasaka et al. | 546/48 |
| 4,894,456 | 1/1990 | Wall et al. | 546/48 |
| 4,914,205 | 4/1990 | Sawada et al. | 546/48 |
| 4,939,255 | 7/1990 | Tagawa et al. | 546/48 |
| 4,943,579 | 7/1990 | Vishnuvajjala et al. | 546/48 |
| 4,981,968 | 1/1991 | Wall et al. | 546/48 |
| 5,004,758 | 4/1991 | Boehm et al. | 546/48 |
| 5,061,795 | 10/1991 | Tagawa et al. | 546/48 |
| 5,061,800 | 10/1991 | Yaegashi et al. | 546/48 |
| 5,106,742 | 4/1992 | Wall et al. | 546/48 |
| 5,112,526 | 6/1992 | Wall et al. | 546/48 |
| 5,162,532 | 11/1992 | Comins et al. | 546/48 |

FOREIGN PATENT DOCUMENTS 57-116074 7/1982 Japan .

OTHER PUBLICATIONS

Krohn et al. (I), Chem. Ber., vol. 108, pp. 3030–3042 (1975).
Krohn et al. (II), Chem. Ber. vol. 109, pp. 1389–1394 (1976).
Fukada, Biochemical Pharmacology, vol. 34(8), pp. 1225–1230 (1985).
Cai et al., The Alkaloids, vol. XXI–Chapter 4 (Academic Press) pp. 101–137 (1983).
Danishefsky, S., and Etheredge, S. J., J. Org. Chem., 39: 3430–3432 (1974); U.S.A.
Giovanella, B. C., et al., Science, 246:1046–1048 (1989); U.S.A.
Hsiang, Y.-H., et al., J. Biol. Chem., 260: 14873–14878 (1985); U.S.A.
Hsiang, Y.-H., and Liu, L. F., Cancer Research, 48:1722–1726 (1988); U.S.A.
T. Kunimoto, et al., Cancer Research, 47: 5944–5947 (1987); U.S.A.

Primary Examiner—Bernard Dentz
Attorney, Agent, or Firm—John P. White

[57] ABSTRACT

Substituted analogues of camptothecin possessing cytotoxic activity towards cancer cells, of the general structure:

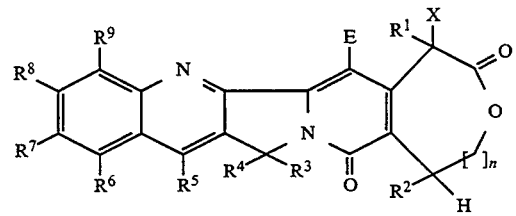

wherein E is H, $CO_2R$, $CONH_2$, $CONHR$, $CONR_2$, acyl, or CN; X is H, OH, or OR; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, C-glycal, nitro, cyano, aminoalkoxy, Cl, F, Br, I, $SR^{10}$, $NR^{11}R^{12}$, or $OR^{13}$; R is H, alkyl, aryl, alkylaryl, hydroxyalkyl, or hydroxyalkyl; $R^{10}$, $R^{11}$ and $R^{12}$ are independently the same or different and are H, alkyl, aryl, alkylaryl, hydroxyalkyl, or acyl; $R^{13}$ is glycosyl; n is 0 or 1; with the proviso that when $R^1$ is ethyl, and n is 0, E, $R^2$, $R^3$, and $R^4$ are not all H. Intermediate compounds leading to the camptothecin analogues comprise substituted tricyclic compounds which consist of rings C, D, and E fused together. Methods for preparing the analogues involve condensation of such intermediates with variably substituted protected α-aminobenzaldehydes.

21 Claims, 8 Drawing Sheets

FIGURE 1B a. Dimethyl sulfate
b. Meldrum's acid, triethylamine, benzene
c. Sodium methoxide, methanol
d. Dimethylallenedicarboxylate, triethylamine
e. Potassium t-butoxide, THF, Ethyl iodide
f. Formaldehyde, acid
g. Hydrobromic acid, reflux
h. Selenium dioxide, 160°C, dioxane
i. Pyridinium dichromate, 0°C
j. o-Aminophenyl toluidine, toluene, tosic acid

Figure 2B k. Selenium dioxide, 160°C, dioxane
l. Pyridinium dichromate, 0°C
m. o-Aminophenyl toluidine, toluene, tosic acid

Figure 3B a. Davis' oxaziridine, KHMDS, THF
b. Pyridinium dichromate, 0°C
c. o-Aminophenyl touluidine, toluene, tosic acid
d. Hydrobromic acid, reflux
e. $CuCl_2$, oxygen, dimethylamine, DMF

Figure 4B a. Davis' oxaziridine, KHMDS, THF
b. Pyridinium dichromate, 0°C
c. o-Aminophenyl toluidine, toluene, tosic acid
d. CuCl$_2$, oxygen, dimethylamine, DMF

5,446,047

CAMPTOTHECIN ANALOGUES

BACKGROUND OF THE INVENTION

This invention relates to new camptothecin analogues useful for the treatment of cancer, to intermediates useful for their synthesis, and to methods of preparing the analogues and intermediates.

Camptothecin (1) is a pentacyclic alkaloid possessing a fused quinoline in rings A and B, a pyrroline in ring C, an α-pyridone in ring D, and a six-membered lactone in ring E, and was first isolated from *Camptotheca acuminata* (Nyssaceae), a tree native to southern China (Wall, et al., *J. Amer. Chem. Soc.*, 88, 3888–3890 (1966)). Promising antitumor and antileukemic activity and extreme rarity of the compound in nature (present in stem bark at abundances of about 0.01% by weight) have motivated extensive studies directed toward the total synthesis of camptothecin as well as the design of analogues intended to exhibit greater activity and lower toxicity than camptothecin itself. The results of these efforts have been comprehensively reviewed (C. R. Hutchinson, *Tetrahedron*, 37, 1047–1065 (1981); A. G. Schultz, *Chemical Rev.*, 73, 385–405 (1973)).

Mechanistic studies of the biological action of camptothecin have pointed to the enzyme topoisomerase I as the main intracellular target of the compound. By binding to and stabilizing a covalent DNA-topoisomerase I complex in which a strand of DNA is broken (R. P. Hertzberg, et al., *J. Med. Chem.*, 32, 715 (1989); W. D. Kingsbury, et al., *J. Med. Chem.*, 34, 98 (1991)), it is believed, camptothecin damages DNA and strongly inhibits the synthesis of nucleic acids in cancer cells. A structure-activity correlation for camptothecin analogues has been established between the anti-cancer activity of an analogue and its ability to stabilize the DNA-topoisomerase I complex. Adding further weight to this belief, cell lines which are resistant to camptothecin have been determined to contain a mutated form of topoisomerase I (R. S. Gupta, et al., *Cancer Res.*, 48, 6404 (1988)).

High toxicity and low solubility have diminished the clinical utility of camptothecin, stimulating a search for derivatives which transcend these limitations. Numerous analogues have been prepared by methods described in previous disclosures. None of these methods, however, offer a general approach for preparing camptothecin analogues with highly variable ring substitution patterns. For example, Miyasaka, et al. (U.S. Pat. No. 4,399,282), disclose camptothecin analogues substituted by an alkyl, aralkyl, alkoxycarbonyl, or alkoxyalkyl group exclusively in the 7-position, while J. C. Boehm, et al. (U.S. Pat. No. 5,004,758), disclose camptothecins substituted at positions 9 and 10, and Miyasaka, et al. (U.S. Pat. No. 4,473,692) provide compounds with certain groups located at positions 5, 7, and 10, but not otherwise. Because of the sparing solubility of camptothecin in many organic solvents, and because of the special characteristic of camptothecin that the aromatic rings are not sufficiently reactive, the usual electrophilic ring substitution reactions may not be performed on the parent structure, thereby making the preparation of many potentially valuable substitution patterns unobvious to one skilled in the chemical art. However, nitration has been effected by Chinese workers (P. Pei-chuang, et al., *Hau Hsueh Hsueh Pao*, 33, 71 (1975); *Chem, Abstr.*, 84, 115629p (1975)) at the 12-position under forcing conditions (nitric acid/sulfuric acid) at the 9-position of a 10,11-methylenedioxycamptothecin (M. E. Wall, et al., U.S. Pat. No. 5,049,668), and at the 10-position by proceeding through a tetrahydrocamptothecin intermediate followed by subsequent re-oxidation (Miyasaka, et al., U.S. Pat. No. 4,473,692), thereby allowing access to a range of substitution but at the cost of starting from precious native camptothecin or its analogues.

Chemical modification of the A, B, and C ring is of greatest therapeutic interest based on previous structure-function studies. However, while most alterations in the D and E rings have depressed biological activity, certain modifications of these rings have been achieved without losing much activity, as disclosed in U.S. Pat. Nos. 3,894,029, 4,031,098, 4,914,205, and 4,943,579. The present invention uniquely allows simultaneous changes in substitution in all rings of camptothecin.

While several syntheses of camptothecin have been disclosed in prior art (for example, E. J. Corey, et al., *J. Amer. Chem. Soc.*, 40, 2140 (1975); J. C. Bradley, et al., *J. Org. Chem.*, 41, 699 (1976); G. Stork, et al., *J. Amer. Chem. Soc.*, 93, 4074 (1971); E. Winterfeld, et al., *Angew. Chem.*, 84, 265 (1972)), the present approach offers the combined advantages of good preparative yield, a minimum number of reaction steps, and synthetic flexibility in the design of derivative analogues of camptothecin. Because of the intense anti-cancer activity of the parent structure and the possibility of obtaining a large variety of analogues, the present invention makes possible the development of a greater number of new target pharmaceuticals with more desirable chemical and clinical properties, including improved solubility, bioavailability, and anticancer activity. The present invention therefore represents a potentially important advance for cancer chemotherapy.

BRIEF DESCRIPTION OF THE DRAWINGS

A more complete understanding of the invention and many of its advantages will become apparent by reference to the detailed description which follows when considered in conjunction with the accompanying drawings, wherein:

FIGS. 1A and 1B illustrate the preparation of native camptothecin via decarboxylation and SeO$_2$-mediated oxygenation and of a de-AB-camptothecin intermediate, according to the invention.

FIGS. 2A and 2B provide the synthesis of 14-carbomethoxysubstituted dl-camptothecin via SeO$_2$-mediated oxygentation of a de-AB-camptothecin intermediate, according to the invention.

FIGS. 3A and 3B show the preparation of native camptothecin via decarboxylation and Davis' oxaziridinemediated oxygenation and of a 14-carbomethoxy-substituted de-AB-camptothecin intermediate, according to the invention.

FIGS. 4A and 4B exemplify the synthesis of 14-carbomethoxy-substituted camptothecin analoguss via Davis' oxaziridine-mediated oxygenation of a de-AB-camptothecin intermediate, according to the invention.

SUMMARY OF THE INVENTION

Figure 1A:
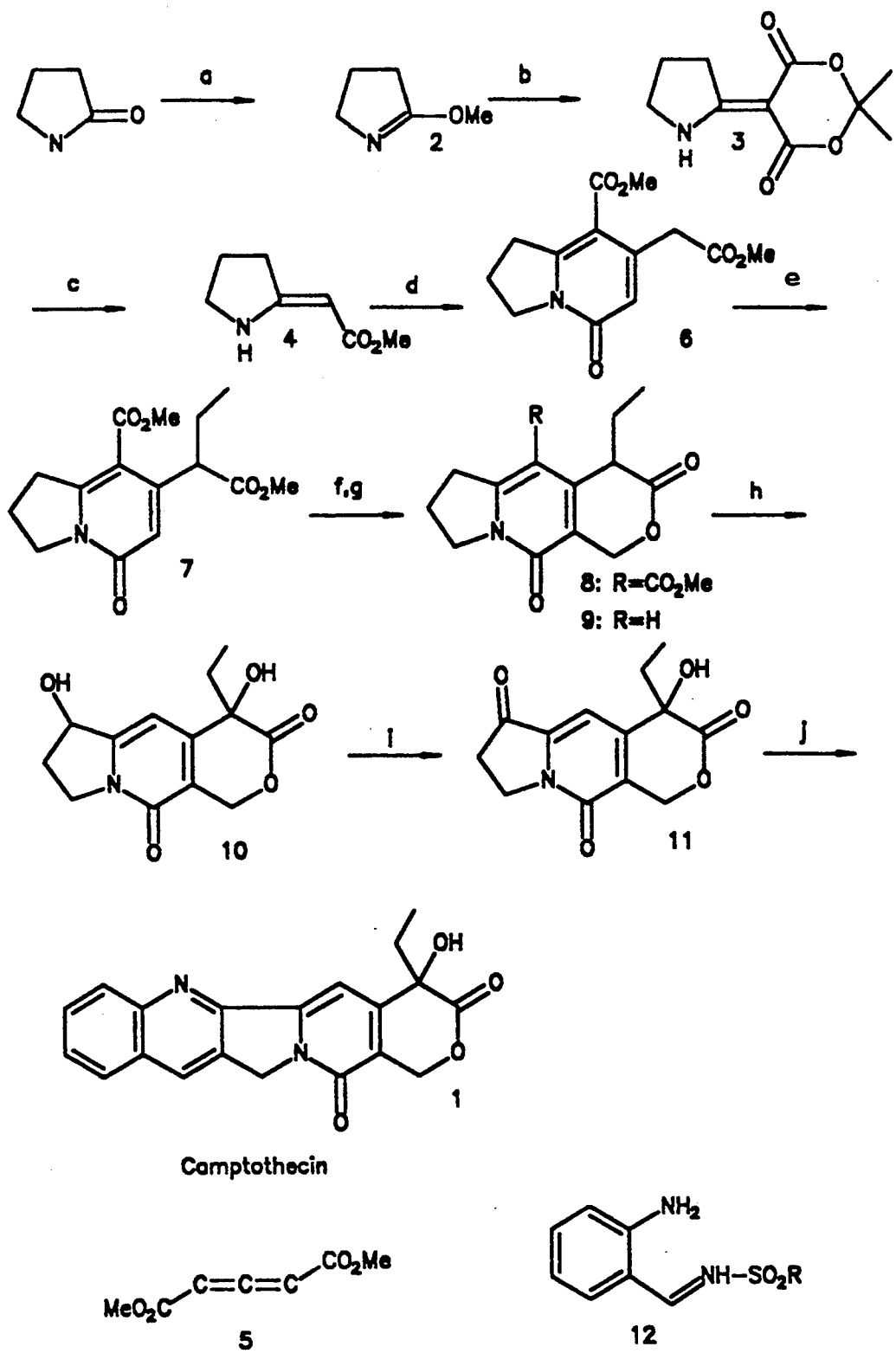
Figure 2A:
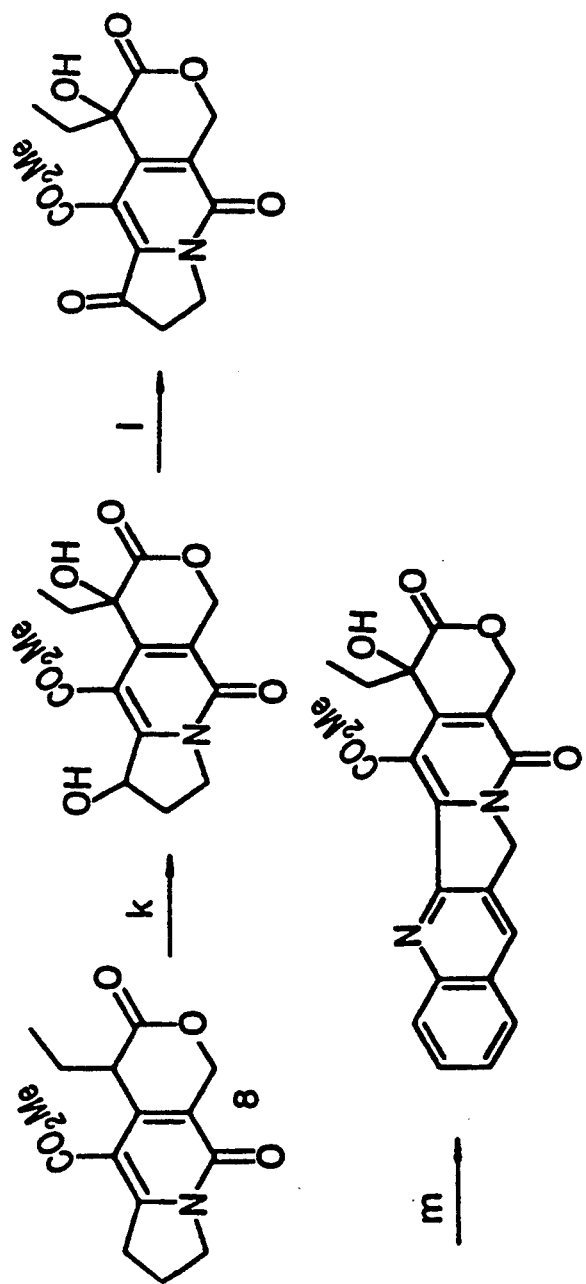
Figure 3A:
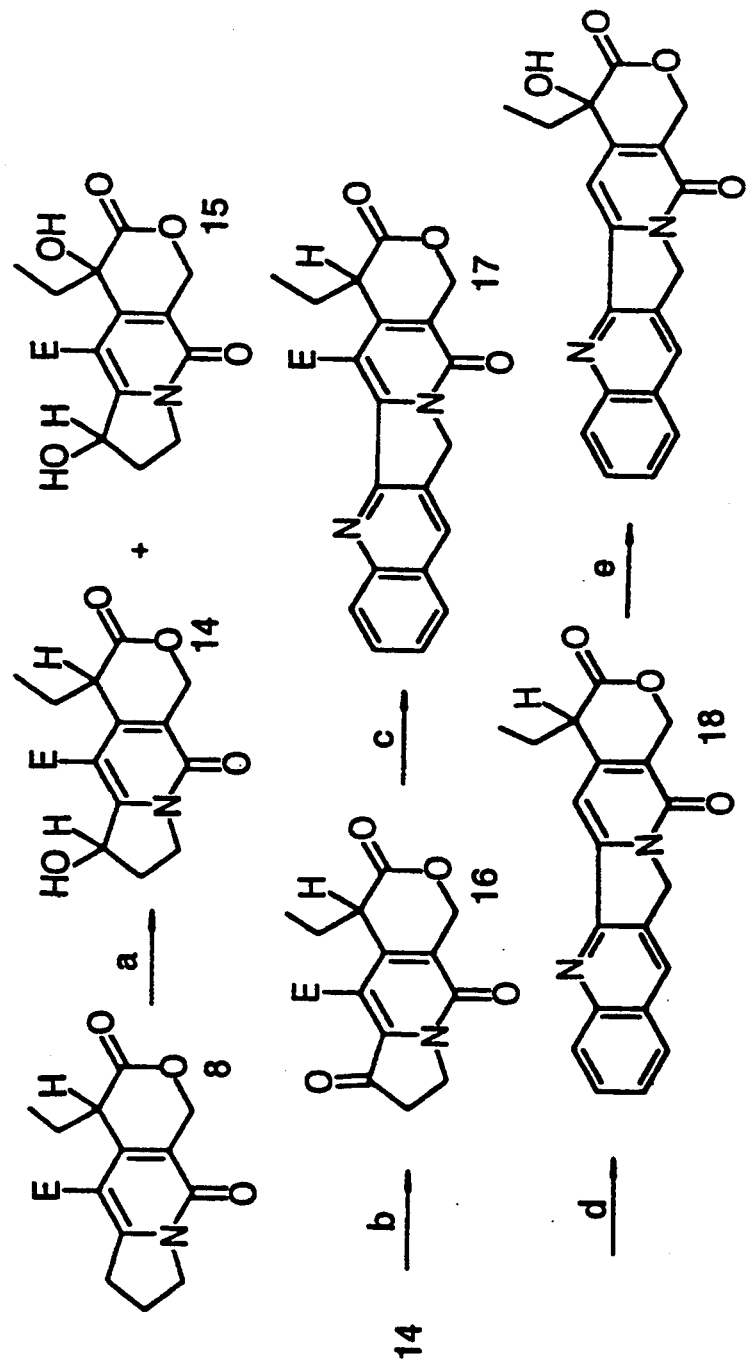
Figure 4A:
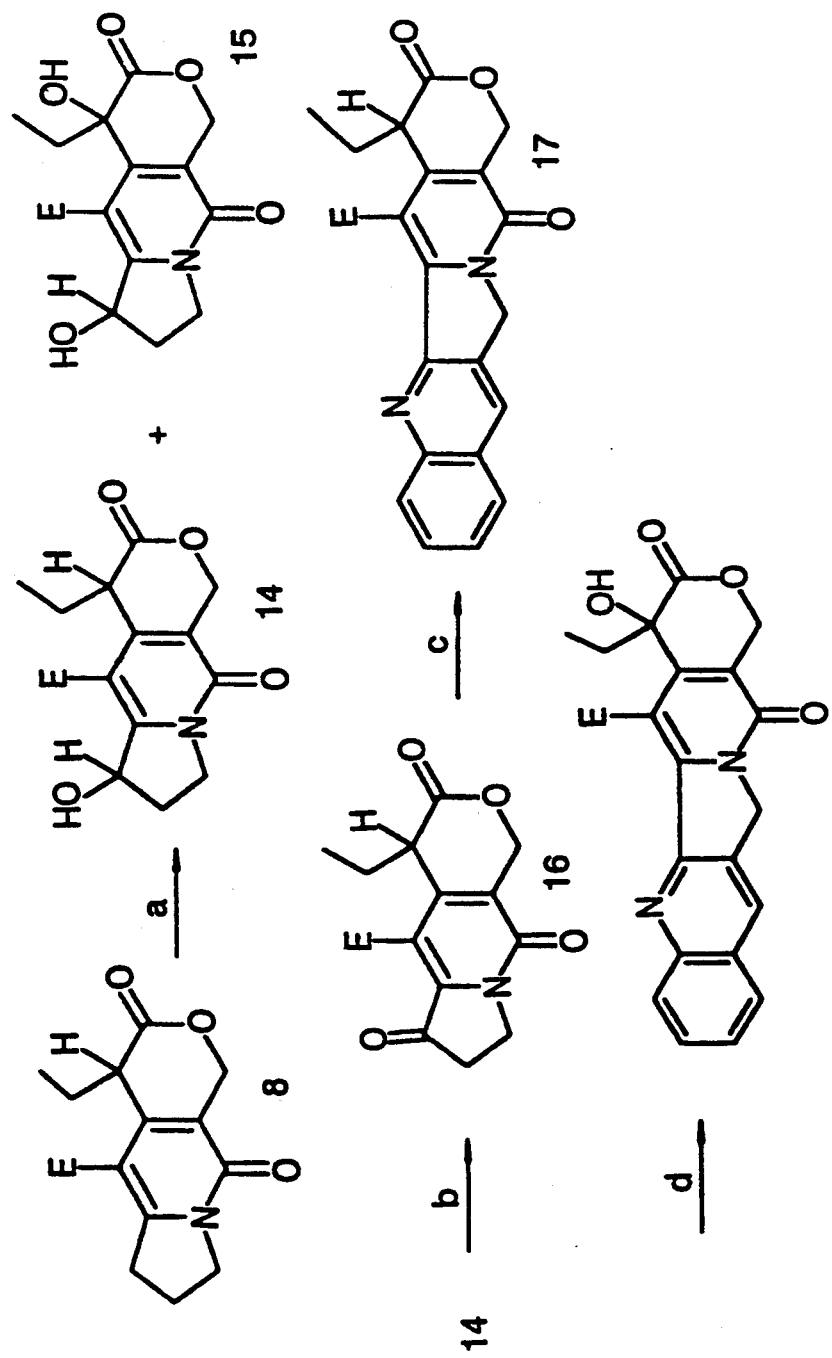

The present invention relates to new substituted analogues of camptothecin bearing one or more groups in the 5-, 7-, 10-, 11-, 12-, 14-, 17-and/or 20-position thereof.

Thus, the present invention provides a compound having the structure:

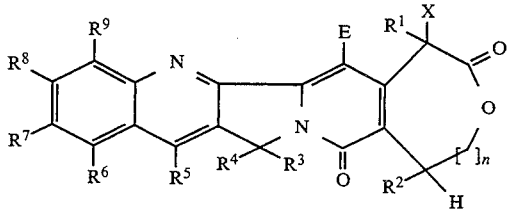

wherein E is H, CO₂R, CONH₂, CONHR, CONR₂, acyl, or CN; X, R¹ is O, or X is H or OH and R¹ is H, linear or branched alkyl, linear or branched alkylaryl, hydroxyalkyl, or aryl; R², R³, and R⁴ are independently the same or different and are H, linear or branched alkyl, linear or branched alkylaryl, hydroxyalkyl, or aryl; R⁵, R⁶, R⁷, R³, and R⁹ are independently the same or different and are H, linear or branched alkyl, linear or branched alkylaryl, aryl, CO₂R, alkoxy, aryloxy, hydroxyalkyl, C-glycal, nitro, cyano, aminoalkoxy, Cl, F, Br, I, SR¹⁰, or NR¹¹R¹², or OR¹³; R is H, alkyl, aryl, alkylaryl, or hydroxyalkyl; R¹⁰, R¹¹ and R¹² are independently the same or different and are H, alkyl, aryl, alkylaryl, or acyl; R¹³ is glycosyl; n is 0 or 1; with the proviso that when R¹ is ethyl, and n is 0, E, R², R³ and R⁴ are not all H. Another object of the invention is to provide key intermediates useful for the preparation of such new analogues of camptothecin.

Thus, the invention also provides a compound having the structure:

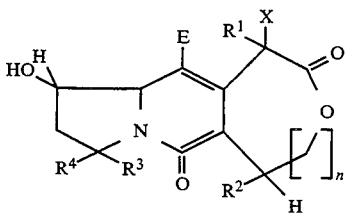

wherein E is H, CO₂R, CONH₂, CONHR, CONR₂, acyl, or CN; X is H, OH, or OR; R¹, R², R³, and R⁴ are independently the same or different and are H, linear or branched alkyl, linear or branched alkylaryl, hydroxyalkyl, or aryl; R is H, alkyl, aryl, alkylaryl, or hydroxyalkyl; with the proviso that when R¹ is ethyl and n is 0, E, R², R³ and R⁴ are not all H.

The invention further provides a compound having the structure:

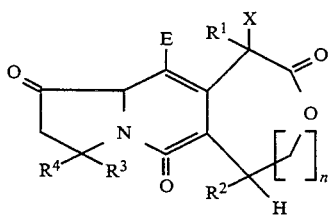

wherein E is H, CO₂R, CONH₂, CONMR, CONR₂, acyl, or CN; X is H, OH, or OR; R¹, R², R³, and R⁴ are independently the same or different and are H, linear or branched alkyl, linear or branched alkylaryl, hydroxyalkyl, or aryl; R is H, alkyl, aryl, alkylaryl, or hydroxyalkyl; with the proviso that when R¹ is ethyl, and n is 0, E, R², R³ and R⁴ are not all H.

An object of the present invention is to provide a process of synthesizing a compound having the structure:

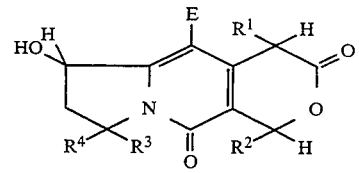

wherein E is H; X is OH; R¹, R², R³, and R⁴ are independently the same or different and are H, linear or branched alkyl, linear or branched alkylaryl, hydroxyalkyl, or aryl; which comprises:

(a) treating the pyrrolidone having the structure:

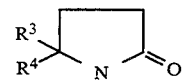

wherein R³ and R⁴ are independently the same or different and are H, linear or branched alkyl, or linear or branched alkylaryl, hydroxyalkyl, or aryl with an alkylating agent under suitable conditions to form a compound having the structure:

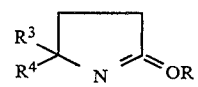

wherein R³ and R⁴ are independently the same or different and are H, linear or branched alkyl, or linear or branched alkylaryl, hydroxyalkyl, or aryl;

(b) condensing the compound formed by step (a) with Meldrum's acid in the presence of a base under conditions suitable to form a compound having the structure:

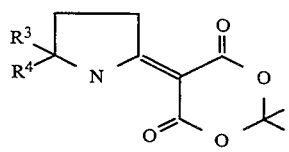

wherein R³ and R⁴ are independently the same or different and are H, linear or branched alkyl, or linear or branched alkylaryl, hydroxyalkyl, or aryl;

(c) treating the compound formed by step (b) with alkali alkoxide under conditions suitable to form a compound having the structure:

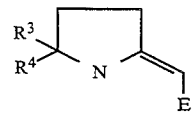

wherein R}and R⁴ are independently the same or different and are H, linear or branched alkyl, or linear or branched alkylaryl, hydroxyalkyl, or aryl; and, E is CO₂R, CONH₂, CONHR, CONR₂, acyl, or CN; R is H, alkyl, aryl, alkylaryl, or hydroxyalkyl;

(d) reacting the compound formed by step (c) with a compound having the structure:

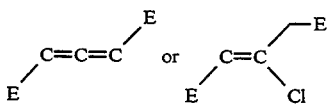

wherein E is $CO_2R$, $CONH_2$, $CONMR$, $CONR_2$, acyl, or CN; and, R is H, alkyl, aryl, alkylaryl, or hydroxyalkyl; under conditions suitable to form a compound having the structure:

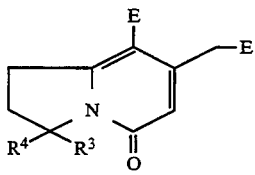

wherein $R^1$ and $R^4$ are independently the same or different and are H, linear or branched alkyl, or linear or branched alkylaryl, hydroxyalkyl, or aryl; E is $CO_2R$, $CONH_2$, $CONHR$, $CONR_2$, acyl, or CN; and, R is H, alkyl, aryl, alkylaryl, or hydroxyalkyl;

(e) deprotonating the compound formed by step (d) with a non-nucleophilic base to form an anion and alkylating the anion with an electrophilic reactant under conditions suitable to form a compound having the structure:

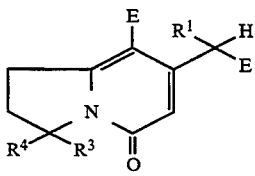

wherein E is $CO_2R$ $CONH_2$, $CONHR$, $CONR_2$, acyl or CN; $R^1$, $R^3$, and $R^4$ are independently the same or different and are H, linear or branched alkyl, linear or branched alkylaryl, hydroxyalkyl, or aryl; and, R is H, alkyl, aryl, alkylaryl, or hydroxyalkyl;

(f) reacting the compound formed by step (e) with a carbonyl compound having the structure $R^2$-CHO, wherein $R^2$ is H, linear or branched alkyl, or linear or branched alkylaryl, hydroxyalkyl, or aryl, under suitable conditions to form a compound having the structure:

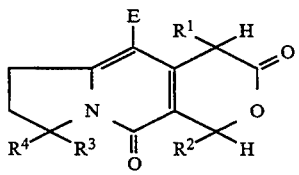

wherein E is $CO_2R$, $CONH_2$, $CONHR$, $CONR_2$, acyl, or CN; $R^1$, $R^2$, $R^3$, and $R^4$ are independently the same or different and are H, linear or branched alkyl, linear or branched alkylaryl, hydroxyalkyl, or aryl; and, R is H, alkyl, aryl, alkylaryl, or hydroxyalkyl;

(g) hydrolyzing and decarboxylating the compound formed by step (f) under suitable acidic conditions to form a compound having the structure:

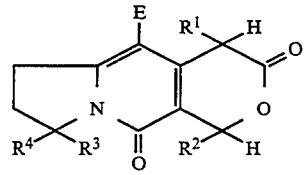

wherein E is H; $R^1$ $R^2$ $R^3$ and $R^4$ are independently the same or different and are H, linear or branched alkyl, linear or branched alkylaryl, hydroxyalkyl, or aryl;

(h) treating the compound formed by step (g) with an hydroxylating reagent under conditions suitable to form the compound having the structure:

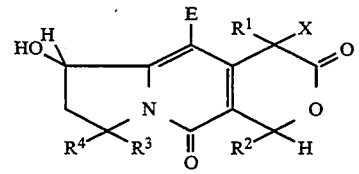

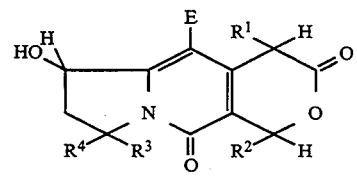

wherein E is H; X is OH; $R^1$, $R^2$, $R^3$ and $R^4$ are independently the same or different and are H, linear or branched alkyl, linear or branched alkylaryl, hydroxyalkyl, or aryl.

DETAILED DESCRIPTION OF THE INVENTION

The present invention provides new analogues of camptothecin, an anti-cancer compound having the structure:

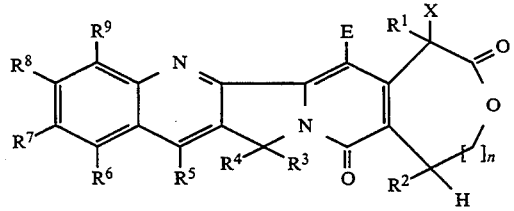

wherein E is H, $CO_2R$, $CONH_2$, $CONHR$, $CONR_2$, acyl, or CN; X, $R^1$ is O, or X is H or OH and $R^1$ is H, linear or branched alkyl, linear or branched alkylaryl, hydroxyalkyl, or aryl; $R^2$m $R^3$ and $R^4$ are independently the same or different and are H, linear or branched alkyl, linear or branched alkylaryl, hydroxyalkyl, or aryl; $R^5$, $R^6$, $R^7$, $R^8$ and $R^9$ are independently the same or different and are H, linear or branched alkyl, linear or branched alkylaryl, aryl, $CO_2R$, alkoxy, aryloxy, hydroxyalkyl, C-glycal, nitro, cyano, aminoalkoxy, Cl, F, Br, I, $SR^{10}$, or $NR^{11}R^{12}$, or $OR^{13}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; $R^{13}$ is glycosyl; n is 0 or 1; with the proviso that when $R^1$ is ethyl, and n is 0, E, $R^2$, $R^3$, and $R^4$ are not all H. In one embodiment of the invention, E is H; in another embodiment, E is $CO_2R$ and R is preferably selected from the group consisting of methyl, ethyl, propyl, butyl, benzyl, and phenyl. In certain embodiments, $R^1$ is ethyl; while in certain other embodiments, $R^2$ is $CH_3$. In certain embodiments, X is preferably OH; while in still other embodiments, X is H.

The invention also provides a tricyclic intermediate useful for preparing camptothecin analogues, which has the structure:

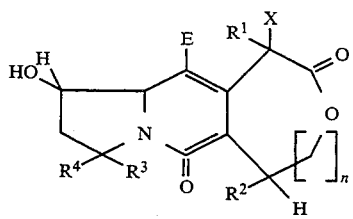

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl; with the proviso that when $R^1$ is ethyl, and n is 0, E, , $R^2$, $R^3$, and $R^4$ are not all H.

The invention further provides another intermediate useful for synthesizing camptothecin analogues having the structure:

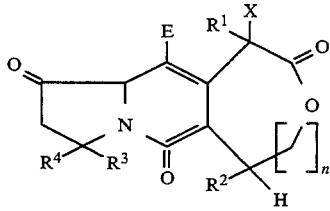

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl; with the proviso that when $R^1$ is ethyl, and n is 0, E, $R^2$, $R^3$, and $R^4$ are not all H.

The invention provides a process of synthesizing the intermediate compound having the structure:

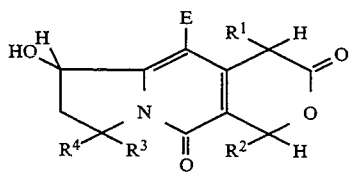

wherein E is H; X is OH; $R^1$, $R^2$, $R^3$, and $R^4$ are independently the same or different and are H, linear or branched alkyl, linear or branched alkylaryl, hydroxyalkyl, or aryl; which comprises:

(a) treating the pyrrolidone having the structure:

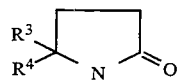

wherein $R^3$ and $R^4$ are independently the same or different and are H, linear or branched alkyl, or linear or branched alkylaryl, hydroxyalkyl, or aryl with an alkylating agent under suitable conditions to form a compound having the structure:

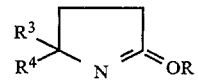

wherein $R^3$ and $R^4$ are independently the same or different and are H, linear or branched alkyl, or linear or branched alkylaryl, hydroxyalkyl, or aryl;

(b) condensing the compound formed by step (a) with Meldrum's acid in the presence of a base under conditions suitable to form a compound having the structure:

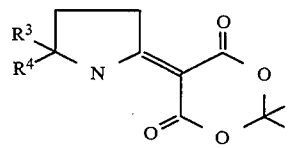

wherein $R^3$ and $R^4$ are independently the same or different and are H, linear or branched alkyl, or linear or branched alkylaryl, hydroxyalkyl, or aryl;

(c) treating the compound formed by step (b) with alkali alkoxide under conditions suitable to form a compound having the structure:

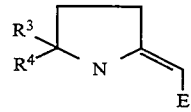

wherein $R^3$ and $R^4$ are independently the same or different and are H, linear or branched alkyl, or linear or branched alkylaryl, hydroxyalkyl, or aryl; and, E is $COaR$, $CONH_2$, CONHR, $CONR_2$, acyl, or CN; R is H, alkyl, aryl, alkylaryl, or hydroxyalkyl;

(d) reacting the compound formed by step (c) with a compound having the structure:

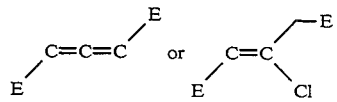

wherein E is $CO_2R$, CONHE, CONHR, CONRE, acyl, or CN; and, R is H, alkyl, aryl, alkylaryl, or hydroxyalkyl; under conditions suitable to form a compound having the structure:

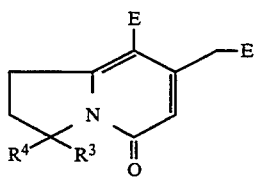

wherein $R^3$ and $R^4$ are independently the same or different and are H, linear or branched alkyl, or linear or branched alkylaryl, hydroxyalkyl, or aryl; E is $CO_2R$, $CONH_2$, CONHR, $CONR_2$, acyl, or CN; and, R is H, alkyl, aryl, alkylaryl, or hydroxyalkyl;

(e) deprotonating the compound formed by step (d) with a non-nucleophilic base to form an anion and alkylating the anion with an electrophilic reactant under conditions suitable to form a compound having the structure:

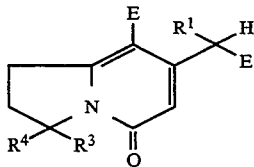

wherein E is $CO_2R$, $CONH_2$, CONHR, $CONR_2$, acyl, or CN; $R^1$, $R^3$, and $R^4$ are independently the same or different and are H, linear or branched alkyl, linear or branched alkylaryl, hydroxyalkyl, or aryl; and, R is H, alkyl, aryl, alkylaryl, or hydroxyalkyl;

(f) reacting the compound formed by step (e) with a carbonyl compound having the structure $R^2$-CHO, wherein $R^2$ is H, linear or branched alkyl, or linear or branched alkylaryl, hydroxyalkyl, or aryl, under suitable conditions to form a compound having the structure:

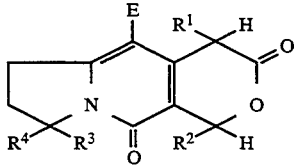

wherein E is $CO_2R$, $CONH_2$, CONHR, $CONR_2$, acyl, or CN; $R^1$, $R^2$ $R^3$, and $R^4$ are independently the same or different and are H, linear or branched alkyl, linear or branched alkylaryl, hydroxyalkyl, or aryl; and, R is H, alkyl, aryl, alkylaryl, or hydroxyalkyl;

(g) hydrolyzing and decarboxylating the compound formed by step (f) under suitable acidic conditions to form a compound having the structure:

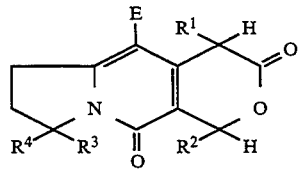

wherein E is H; $R^1$, $R^2$, $R^3$, and $R^4$ are independently the same or different and are H, linear or branched alkyl, linear or branched alkylaryl, hydroxyalkyl, or aryl;

(h) treating the compound formed by step (g) with an hydroxylating reagent under conditions suitable to form the compound having the structure:

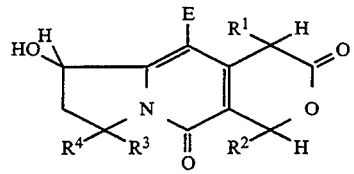

wherein E is H; X is OH; $R^1$, $R^2$, $R^3$, and $R^4$ are independently the same or different and are H, linear or branched alkyl, linear or branched alkylaryl, hydroxyalkyl, or aryl.

The process of step (a) above may be effected using a variety of alkylating reagents, known to those skilled in the art, but is preferably dimethyl sulfate. The process of step (b) results on heating the lactim ether with an active methylene condensing agent, preferably Meldrum's acid, in the presence of a tertiary amine base in an inert solvent such as benzene, at a temperature sufficient to cause reaction, preferably at the reflux temperature. The condensation product is then converted in process step (c) to the unsaturated decarboxylated product by heating the product of step (b) with an alkali metal alkoxide or aryloxide in its corresponding alcohol as solvent or cosolvent at a temperature sufficient to cause reaction, preferably at the reflux temperature of the solvent. Process step (d) may be effected by treating the decarboxylated product with a disubstituted allene in the presence of a tertiary organic base, preferably triethylamine, in an alcoholic solvent, preferably absolute ethanol, at a temperature sufficient to cause reaction, preferably at room temperature. The reaction takes from 40 to 80 hours, and most usually about 65 hours. The resulting pyridone is deprotonated in step (e) using a non-nucleophilic base, preferably potassium tbutoxide, in an anhydrous dipolar solvent, such as dimethyoxyethane, at a temperature adequate to cause reaction, but low enough to prevent side-reactions, preferably at $-78°$ C. The resulting deprotonated species is then alkylated or arylated with an electrophilic reagent, most commonly an alkyl halide, tosylate, or aryne intermediate, but preferably a primary or secondary alkyl bromide or iodide, and may be driven to completion by warming the reaction mixture to room temperature and stirring for a time depending on the specific alkylating agent, but usually between 2 and 50 hours. Step (f) entails heating the alkylated heterocyclic compound with an alkyl or aryl aldehyde in the presence of an acid catalyst, preferably an organic sulfonic acid or a mineral acid, more preferably concentrated sulfuric acid, in a solvent inert to the reaction conditions, preferably aqueous dioxane. The reaction is preferably carried out in a thick wall tube or other high-pressure reaction vessel, at a temperature sufficient to cause reaction, generally between 90° C. and 160° C., and preferably at 107° C, for about 24 hours. The process of step (g) may be effected by heating a mixture of the lactone formed in step (f) in a mineral acid, preferably concentrated aqueous hydrobromic acid, at a temperature sufficient to produce the desired product, generally between preferably between 90° C. and 140° C., and more preferably at 105° C., for about 18 hours. The process of hydroxylating step (h) is accomplished by heating a mixture of the product of step (g) in a solvent inert to the reaction conditions, such as aqueous dioxane, with an hydroxylating reagent, preferably seleniumdioxide, at a temperature sufficient to cause reaction, but not to degrade the starting material, preferably between 120° C. and 180° C., more preferably at 155° C.

The invention also provides a process of synthesizing camptothecin analogues having the structure:

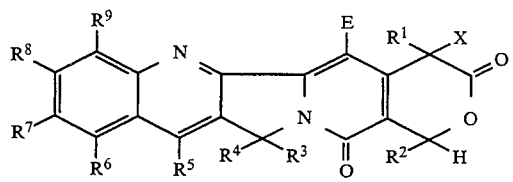

wherein E is H; X is OH; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

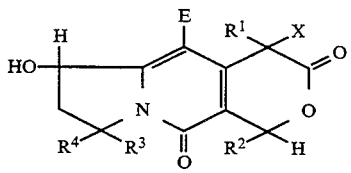

wherein E is H; X is OH; and, $R^1$, $R^2$, $R^3$, and $R^4$ are independently the same or different and are H, linear or branched alkyl, linear or branched alkylaryl, hydroxyalkyl, or aryl; as described above;

(b) oxidizing he compound formed in step (a) with an oxidant under suitable conditions to form a compound having the structure:

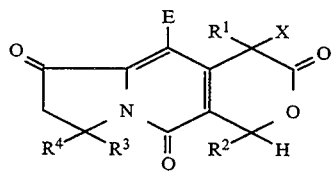

wherein E is H; X is OH; $R^1$, $R^2$, $R^3$ and $R^4$ are independently the same or different and are H, linear or branched alkyl, linear or branched alkylaryl, hydroxyalkyl, or aryl;

(c) condensing the compound formed by step (b) with a compound having structure:

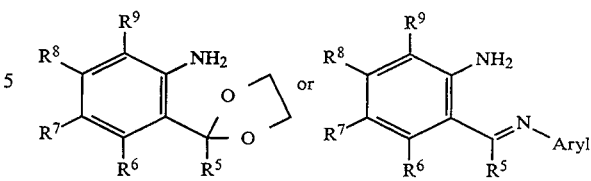

wherein $R^5$, $R^6$, $R^7$, $R^8$ and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; under suitable conditions to form the compound having the structure:

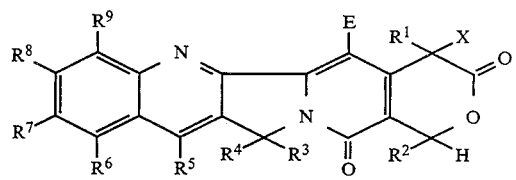

wherein E is H; X is OH; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl alkylaryl or hydroxyalkyl; $R^{11}R^{12}$ and $R^{12}$ are independently the same or different and are H, alkyl, aryl, alkylaryl, or acyl.

The invention provides a process of synthesizing substituted analogues of camptothecin, a compound having the structure:

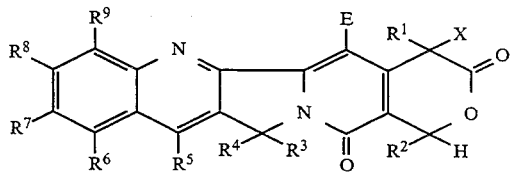

wherein E is H; X is OH; $R^1$, $R^2$, $R^3$ and $R^4$ are independently the same or different and are H, linear or branched alkyl, linear or branched alkylaryl hydroxyalkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

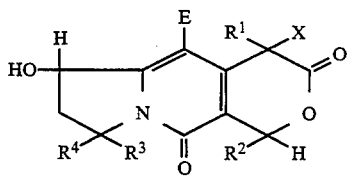

wherein E is H; X is OH; and, $R^1$, $R^2$, $R^3$, and $R^4$ are independently the same or different and are H, linear or branched alkyl, linear or branched alkylaryl, hydroxyalkyl, or aryl; as described above;

(b) oxidizing the compound formed in step (a) with an oxidant under suitable conditions to form a compound having the structure:

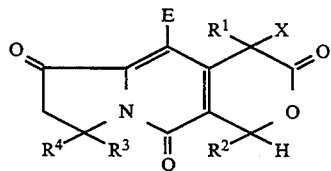

wherein E is H; X is OH; $R^1$, $R^2$, $R^3$, and $R^4$ are independently the same or different and are H, linear or branched alkyl, linear or branched alkylaryl, hydroxyalkyl, or aryl;

(c) condensing the compound formed by step (b) with a compound having structure:

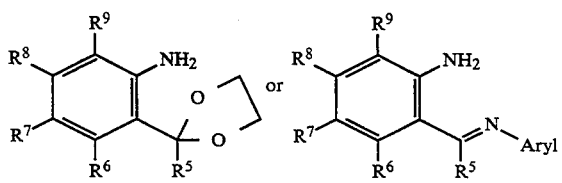

wherein $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; under suitable conditions to form the compound having the structure:

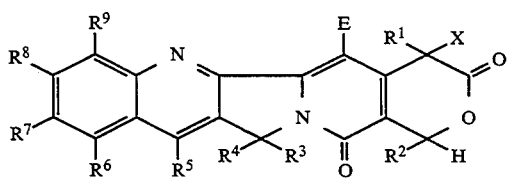

wherein E is H; X is OH; $R^1$, $R^2$, $R^3$ and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl.

The process of step (b) is best performed using the oxidant pyridinium dichromate in the presence of activated powdered A molecular sieves in an inert solvent such as methylene dichloride at a temperature sufficient to result in the desired reaction, usually between −20° C. and 40° C., but preferably about 0° C. The condensation of step (c) is carried out by mixing the tricyclic ketone generated by step (a) with a protected ortho-amino aldehyde or ketone in an inert solvent, such as benzene or toluene, and heating to the reflux temperature of the solvent in the presence of an acid or basic catalyst. Acidic Catalysts include mineral acids, such as sulfuric acid, nitric acid, phosphoric acid, and hydrochloric acid, organic alkanoic and sulfonic acids, such as acetic acid or propionic acid. The preferred catalyst is a mild acid, such as toluenesulfonic acid. A large variety of ortho-amino aldehydes and ketones are available from commercial sources, allowing the preparation of many substitution patterns, while other ortho-amino aldehydes and ketones can be prepared by methods well-known in the art. The reaction is carried out in a solvent inert to the reaction. Aromatic solvents are particularly well suited to the purpose, including benzene and toluene. When the solvent is not miscible with water, the reaction is best effected by azeotropic trapping of water generated in the process.

The invention also provides a process of synthesizing intermediates useful for preparing camptothecin analogues having the structure:

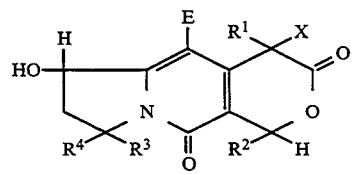

wherein E is $CO_2R$, $CONH_2$, CONHR, $CONR_2$, acyl, or CN; X is OH; $R^1$, $R^2$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl; which comprises:

(a) preparing a compound having the structure:

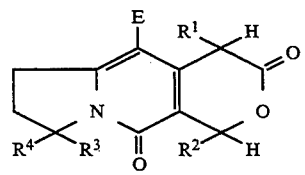

wherein E is $CO_2R$, $CONH_2$, CONHR, $CONR_2$, acyl, or CN; $R^1$, $R^2$, $R^3$, and $R^4$ are independently the same or different and are H, linear or branched alkyl, linear or branched alkylaryl, hydroxyalkyl, or aryl; and, R is H, alkyl, aryl, alkylaryl, or hydroxyalkyl; as described above; and, (b) treating the compound formed in step (a) with an hydroxylating reagent under suitable conditions to form the compound having the structure:

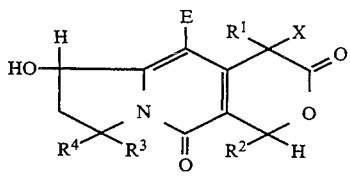

wherein E is CO$_2$R, CONH$_2$, CONMR, CONR$_2$, acyl, or CN; X is OH; R$^1$, R$^2$, R$^3$, and R$^4$ are independently the same or different and are H, linear or branched alkyl, linear or branched alkylaryl, hydroxyalkyl, or aryl; and, R is H, alkyl, aryl, alkylaryl, or hydroxyalkyl.

The process of the preparing step (a) is carried out as described above. The process of the treating step (b) may be accomplished by heating a mixture of the product of preparing step (a) in a solvent inert to the reaction conditions, such as aqueous dioxane, with an hydroxylating reagent, preferably selenium dioxide, at a temperature sufficient to cause reaction, but not to degrade the starting material, preferably between 120° C. and 180° C., more preferably at 155° C.

The invention also provides a process of synthesizing tricyclic intermediates useful for preparing camptothecin analogues. The intermediates have the structure:

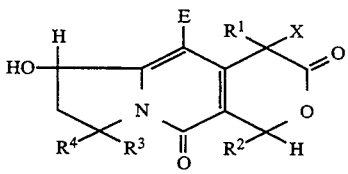

wherein E is CO$_2$R, CONH$_2$, CONHR, CONR$_2$, acyl, or CN; X is OH; R$^1$, R$^2$, R$^3$, and R$^4$ are independently the same or different and are H, linear or branched alkyl, linear or branched alkylaryl, hydroxyalkyl, or aryl; R is H, alkyl, aryl, alkylaryl, or hydroxyalkyl; which comprises:

(a) preparing a compound having the structure:

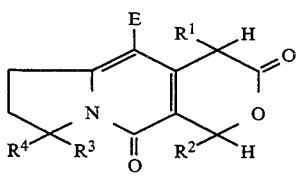

wherein E is CO$_2$R, CONH$_2$, CONMR, CONR$_2$, acyl, or CN; R$^1$, R$^2$, R$^3$, and R$^4$ are independently the same or different and are H, linear or branched alkyl, linear or branched alkylaryl, hydroxyalkyl, or aryl; and, R is H, alkyl, aryl, alkylaryl, or hydroxyalkyl; as described above; and, (b) treating the compound formed in step (a) with an hydroxylating reagent under suitable conditions to form the compound having the structure:

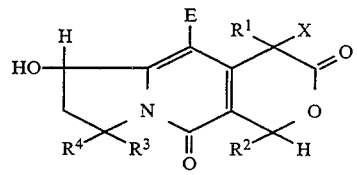

wherein E is CO$_2$R, CONH$_2$, CONHR, CONR$_2$, acyl, or CN; X is OH; R$^1$, R$^2$, R$^3$, and R$^4$, are independently the same or different and are H, linear or branched alkyl, linear or branched alkylaryl, hydroxyalkyl, or aryl; and, R is H, alkyl, aryl, alkylaryl, or hydroxyalkyl.

The invention provides another variant process of synthesizing camptothecin analogues having the structure:

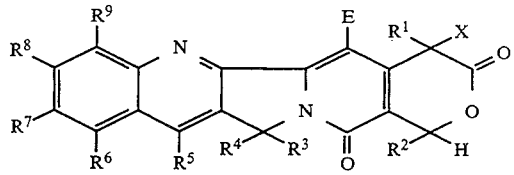

wherein E is CO$_2$R, CONH$_2$, CONHR, CONR$_2$, acyl, or CN; X is OH; R$^1$, R$^2$, R$^3$, and R$^4$ are independently the same or different and are H, linear or branched alkyl, linear or branched alkylaryl, hydroxyalkyl, or aryl; R$^5$, R$^6$, R$^7$, R$^8$, and R$^9$ are independently the same or different and are H, linear or branched alkyl, linear or branched alkylaryl, aryl, CO$_2$R, alkoxy, aryloxy, hydroxyalkyl, nitro, cyano, aminoalkoxy, Cl, F, Br, I, SRR$^{10}$ NR$^{11}$R$^{12}$; R is H, alkyl, aryl, alkylaryl, or hydroxyalkyl; R$^{10}$, R$^{11}$ and R$^{12}$ are independently the same or different and are H, alkyl, aryl, alkylaryl, or acyl; which comprises:

(a) preparing a compound having the structure:

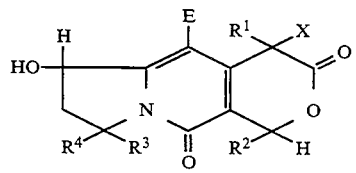

wherein E is CO,R, CONH$_2$, CONHR, CONR$_2$, acyl, or CN; X is OH; R$^1$, R$^2$, R$^3$, and R$^4$ are independently the same or different and are H, linear or branched alkyl, linear or branched alkylaryl, hydroxyalkyl, or aryl; R is H, alkyl, aryl, alkylaryl, or hydroxyalkyl; as described above;

(b) oxidizing the compound formed in step (a) with an oxidant under suitable conditions to provide a compound having the structure:

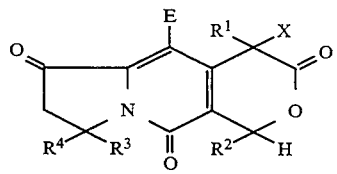

wherein E is CO$_2$R, CONH$_2$, CONHR, CONR$_2$, acyl, or CN; X is OH; R$^1$, R$^2$, R$^3$, and R$^4$ are independently the same or different and are H, linear or branched alkyl, linear or branched alkylaryl, hydroxyalkyl, or aryl; R is H, alkyl, aryl, alkylaryl, or hydroxyalkyl; and, (c) condensing the compound formed by step (d) with a compound having structure:

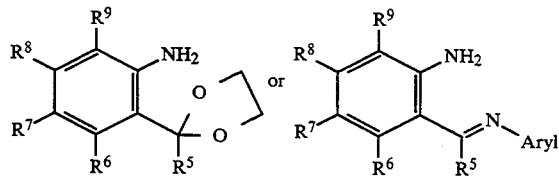

wherein $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$ or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; under suitable conditions to form the compound having the structure:

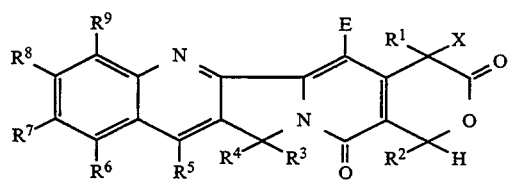

wherein E is $CO_2R$, $CONH_2$, $CONMR$, $CONR_2$, acyl, or CN; X is OH; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; and, $R^{10}$, $R^{11}$ and $R^{12}$ are independently the same or different and are H, alkyl, aryl, alkylaryl, or acyl.

The process of the oxidizing step (b) is best effected using pyridinium dichromate in the presence of powdered 4A molecular sieves in an inert solvent such as methylene dichloride at 0°-5° C.

The invention further provides a process of synthesizing a compound having the structure:

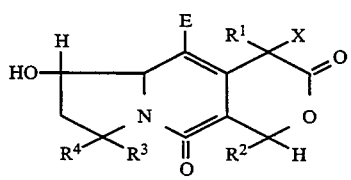

wherein E is H, $COaR$, $CONH_2$, $CONHR$, $CONR_2$, acyl, or CN; X is H or OH; $R^1$, $R^2$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl; which comprises:

(a) preparing a compound having the structure:

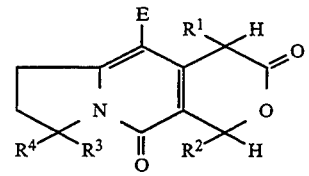

wherein E is H $CO_2R$, $CONH_2$, $CONHR$, $CONR_2$, acyl, or CN; $R^1$, $R^2$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl; as described above; and, (b) treating the compound formed in step (a) with an hydroxylating agent comprising potassium hexamethyldisilamide and a reagent having the structure:

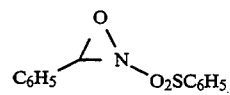

under suitable conditions to form the compound having the structure:

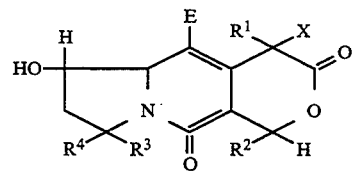

wherein E is H, $CO_2R$, $CONH_2$, $CONHR$, $CONR_2$, acyl, or CN; X is H or OH; $R^1$, $R^2$, $R^3$ and $R^4$ are independently the same or different and are H, linear or branched alkyl, linear or branched alkylaryl, hydroxyalkyl, or aryl; R is H, alkyl, aryl, alkylaryl, or hydroxyalkyl.

The invention also provides a process of synthesizing a compound having the structure:

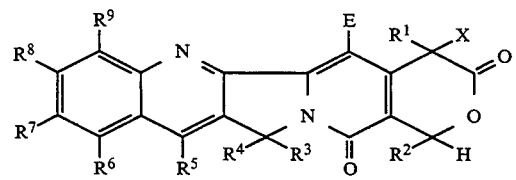

wherein E is H, $CO_2R$, $CONH_2$, $CONHR$, $CONR_2$, acyl, or CN; X is H; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^3$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

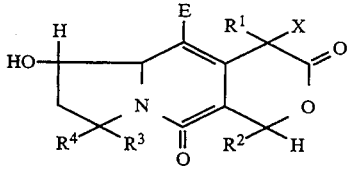

wherein E is H, CO$_2$R, CONH$_2$, CONHR, CONR$_2$, acyl, or CN; X is H; R$^1$, R$^2$, R$^3$, and R$^4$ are independently the same or different and are H, linear or branched alkyl, linear or branched alkylaryl, hydroxyalkyl, or aryl; R is H, alkyl, aryl, alkylaryl, or hydroxyalkyl; as described above;

(b) oxidizing the compound formed in step (a) under suitable conditions with an oxidant to provide a compound having the structure:

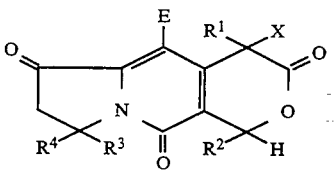

wherein E is H, CO$_2$R, CONH$_2$, CONHR, CONR$_2$, acyl, or CN; X is H; R$^1$, R$^2$, R$^3$, and R$^4$ are independently the same or different and are H, linear or branched alkyl, linear or branched alkylaryl, hydroxyalkyl, or aryl; R is H, alkyl, aryl, alkylaryl, or hydroxyalkyl; and, (c) condensing the compound formed by step (b) with a compound having structure:

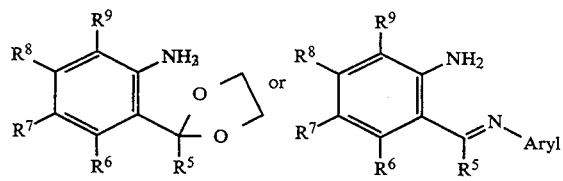

wherein R$^5$, R$^6$, R$^7$, R$^3$, and R$^9$ are independently the same or different and are H, linear or branched alkyl, linear or branched alkylaryl, aryl, CO$_2$R, alkoxy, aryloxy, hydroxyalkyl, nitro, cyano, aminoalkoxy, Cl, F, Br, I, ,SR$^{10}$, or NR$^{11}$R$^{12}$; R is H, alkyl, aryl, alkylaryl, or hydroxyalkyl; R$^{10}$, R$^{11}$ and R$^{12}$ are independently the same or different and are H, alkyl, aryl, alkylaryl, or acyl; under suitable conditions to form the compound having the structure:

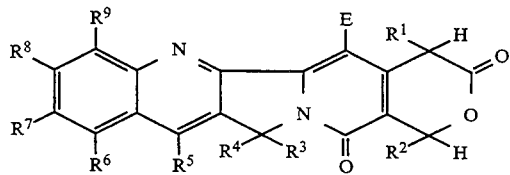

wherein E is H, CO$_2$R, CONH$_2$, CONHR, CONR$_2$, acyl, or CN; R$^1$, R$^2$, R$^3$, and R$^4$ are independently the same or different and are H, linear or branched alkyl, linear or branched alkylaryl, hydroxyalkyl, or aryl; R$^5$, R$^6$, R$^7$, R$^8$, and R$^9$ are independently the same or different and are H, linear or branched alkyl, linear or branched alkylaryl, aryl, CO$_2$R, alkoxy, aryloxy, hydroxyalkyl, nitro, cyano, aminoalkoxy, Cl, F, Br, I, SR$^{10}$, or NR$^{11}$R$^{12}$; R is H, alkyl, aryl, alkylaryl, or hydroxyalkyl; and, R$^{10}$, R$^{11}$ and R$^{12}$ are independently the same or different and are H, alkyl, aryl, alkylaryl, or acyl.

The invention provides a process of synthesizing a compound having the structure:

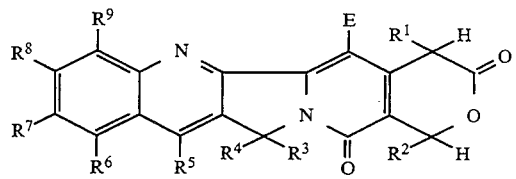

wherein E is H; R$^1$, R$^2$, R$^3$, and R$^4$ are independently the same or different and are H, linear or branched alkyl, linear or branched alkylaryl, hydroxyalkyl, or aryl; R$^5$, R$^6$, R$^7$, R$^8$, and R$^9$ are independently the same or different and are H, linear or branched alkyl, linear or branched alkylaryl, aryl, CO$_2$R, alkoxy, aryloxy, hydroxyalkyl, nitro, cyano, aminoalkoxy, Cl, F, Br, I, SR$^{10}$, or NR$^{11}$R$^{12}$; R is H, alkyl, aryl, alkylaryl, or hydroxyalkyl; R$^{10}$ R$^{11}$ and R$^{12}$ are independently the same or different and are H, alkyl, aryl, alkylaryl, or acyl; which comprises:

(a) preparing a compound having the structure:

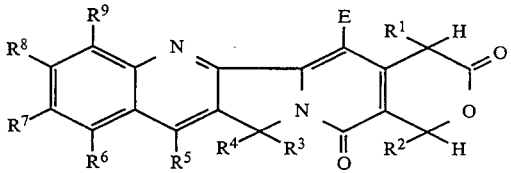

wherein R is H, CO$_2$R, CONH$_2$, CONH$_2$, CONR$_2$, acyl, or CN; R$^1$, R$^2$, R$^3$, and R$^4$ are independently the same or different and are H, linear or branched alkyl, linear or branched alkylaryl, hydroxyalkyl, or aryl; R is H, alkyl, aryl, alkylaryl, or hydroxyalkyl; as described above;

(b) hydrolyzing and decarboxylating the compound formed in step (a) under suitable conditions with an acid to provide a compound having the structure:

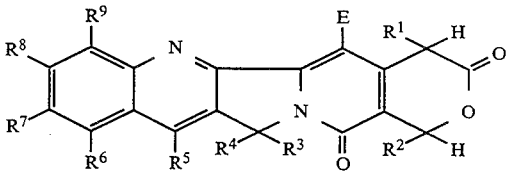

wherein E is H; R$^1$, R$^2$, R$^3$, and R$^4$ are independently the same or different and are H, linear or branched alkyl, linear or branched alkylaryl, hydroxyalkyl, or aryl; R$^5$, R$^6$, R$^7$, R$^8$, and R$^9$ are independently the same or different and are H, linear or branched alkyl, linear or branched alkylaryl, aryl, CO$_2$R, alkoxy, aryloxy, hydroxyalkyl, nitro, cyano, aminoalkoxy, Cl, F, Br, I, SR$^{10}$, or NR$^{11}$R$^{12}$; R is H, alkyl, aryl, alkylaryl, or hydroxyalkyl; R$^{10}$, R$^{11}$ and R$^{12}$ are independently the same or different and are H, alkyl, aryl, alkylaryl, or acyl.

The process of the hydrolyzing and decarboxylating step (b) is accomplished by mixing the product of the preparing step (a) with an acid, preferably an aqueous mineral acid, especially hydrobromic acid, in a sealed tube or high-pressure reaction vessel, and heating at a temperature between 100° C. and 180° C., preferably at 140° C., for 10 to 24 hours, preferably for 15 hours.

The invention also provides a process of synthesizing a compound having the structure:

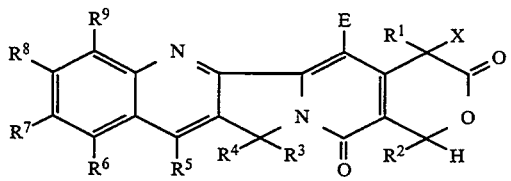

wherein E is H; X is OH; $R^1$, $R^2$, $R^3$ and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

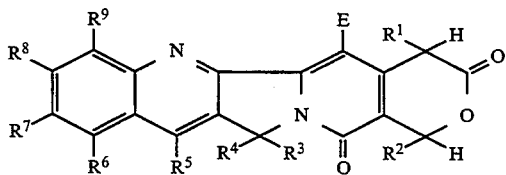

wherein E is H; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$ and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; as described above;

(b) treating the compound formed in step (a) with a hydroxylating reagent under suitable conditions to form a compound having the structure:

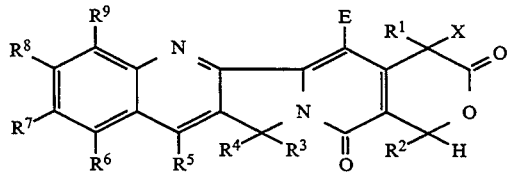

wherein E is H; X is OH; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl aryl, alkylaryl, or hydroxyalkyl; $R^{10}$, $R^{11}$ and $R^{12}$ are independently the same or different and are H, alkyl, aryl, alkylaryl, or acyl.

The treating step (b) is effected by dissolving the product of the preparing step (a) in a dipolar solvent, preferably dimethyformamide, and then adding a hydroxylating reagent containing a divalent ionic metal halide, preferably cupric chloride, and a base, preferably an organic base, such as dimethylamine, and then bubbling in oxygen gas over a period of time sufficient to cause completion of the process, typically about seven hours.

The invention further encompasses a process of synthesizing a compound having the structure:

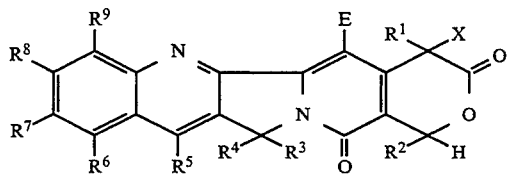

wherein E is $CO_2R$, $CONH_2$, CONMR, $CONR_2$, acyl, or CN; X is OH; $R^1$, $R^2$, $R^3$ and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

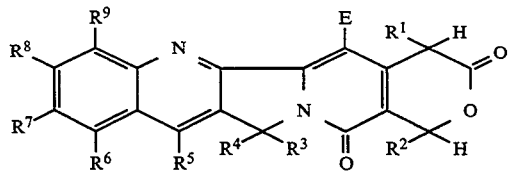

wherein E is $CO_2R$, $CONH_2$, CONHR, $CONR_2$, acyl, or CN; $R^1$, $R^2$, $R^3$, and $R^4$ are independently the same or different and are H, linear or branched alkyl, linear or branched alkylaryl, hydroxyalkyl, or aryl; $R^5$, $R^6$, $R^2$, $R^3$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; as described above;

(b) treating the compound formed in step (a) with a hydroxylating reagent under suitable conditions to form a compound having the structure:

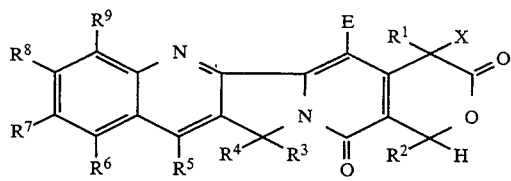

wherein E is CO₂R, CONH₂, CONHR, CONR₂, acyl, or CN; X is OH; R¹, R², R³, and R⁴ are independently the same or different and are H, linear or branched alkyl, linear or branched alkylaryl, hydroxyalkyl, or aryl; R⁵, R⁶, R⁷, R⁸, and R⁹ are independently the same or different and are H, linear or branched alkyl, linear or branched alkylaryl, aryl, CO₂R, alkoxy, aryloxy, hydroxyalkyl, nitro, cyano, aminoalkoxy, Cl, F, Br, I, SR¹⁰, or NR¹¹R¹²; R is H, alkyl, aryl, alkylaryl, or hydroxyalkyl; R¹⁰, R¹¹ and R¹² are independently the same or different and are H, alkyl, aryl, alkylaryl, or acyl. The hydroxylating reagent of the treating step (b) preferably comprises oxygen, cupric halide, and a base.

The invention also includes a process of synthesizing a compound having the structure:

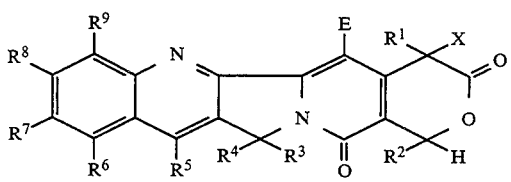

wherein E is H; X is OH; R¹, R², R³, and R⁴ are independently the same or different and are H, linear or branched alkyl, linear or branched alkylaryl, hydroxyalkyl, or aryl; R⁵, R⁶, R⁷, R⁸, and R⁹ are independently the same or different and are H, linear or branched alkyl, linear or branched alkylaryl, aryl, CO₂R, alkoxy, aryloxy, hydroxyalkyl, nitro, cyano, aminoalkoxy, Cl, F, Br, I, SR¹⁰, or NR¹¹R¹²; R is H, alkyl, aryl, alkylaryl, or hydroxyalkyl; R¹⁰, R¹¹ and R¹² are independently the same or different and are H, alkyl, aryl, alkylaryl, or acyl; which comprises:

(a) preparing a compound having the structure:

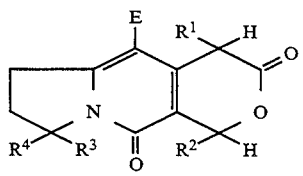

wherein E is H; R¹, R², R³, and R⁴ are independently the same or different and are H, linear or branched alkyl, linear or branched alkylaryl, hydroxyalkyl, or aryl; as described above;

(b) treating the compound formed in step (a) with a hydroxylating reagent under conditions suitable to form the compound having the structure:

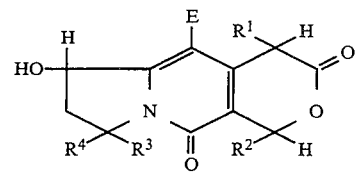

wherein E is H; R¹, R², R³, and R⁴ are independently the same or different and are H, linear or branched alkyl, linear or branched alkylaryl, hydroxyalkyl, or aryl;

(c) oxidizing the compound formed in step (b) with an oxidant under suitable conditions to form the compound having structure:

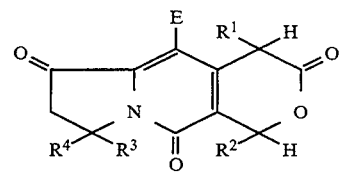

wherein E is H; R¹, R², R³, and R⁴ are independently the same or different and are H, linear or branched alkyl, linear or branched alkylaryl, hydroxyalkyl, or aryl;

(d) condensing the compound formed in step (c) with a compound having structure:

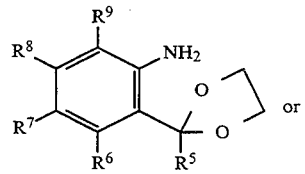

or

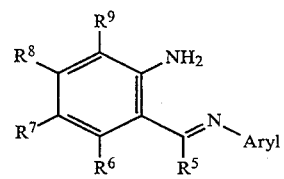

wherein R⁵, R⁶, R⁷, R⁸, and R⁹ are independently the same or different and are H, linear or branched alkyl, linear or branched alkylaryl, aryl, CO₂R, alkoxy, aryloxy, hydroxyalkyl, nitro, cyano, aminoalkoxy, Cl, F, Br, I, , SR¹⁰ or NR¹¹R¹²; R is H, alkyl, aryl, alkylaryl, or hydroxyalkyl; R¹⁰, R¹¹ and R¹² are independently the same or different and are H, alkyl, aryl, alkylaryl, or acyl; under suitable conditions to form a compound having the structure:

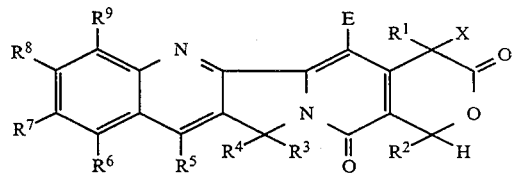

wherein E is H; X is H; R¹, R², R³, and R⁴ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; under suitable conditions to form the compound having the structure:

(e) treating the compound formed in step (d) with a hydroxylating reagent under suitable conditions to form the compound having the structure:

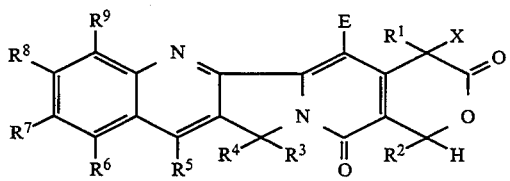

wherein E is H; X is OH; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl. In one embodiment of the invention, the hydroxylating reagent of the treating step (b) comprises potassium hexamethyldisilamide and a reagent having the structure:

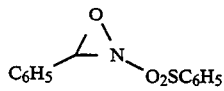

The invention also includes a process of synthesizing a compound having the structure:

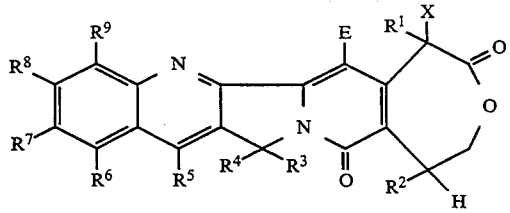

wherein E is $CO_2R$, $CONH_2$, CONHR, $CONR_2$, acyl, or CN; X is OH; $R^1$, $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

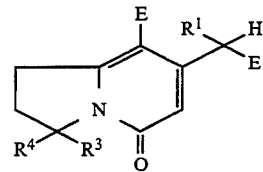

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl; as described above;

(b) halogenating the compound formed in step (a) with a halogenating agent, selected from the group comprising bromine, chlorine, and iodine under suitable conditions to form a compound having the structure:

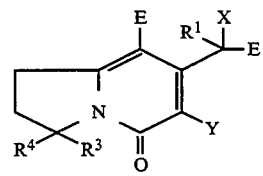

wherein E is $CO_2R$, $CONH_2$, CONHR, $CONR_2$, acyl, or CN; X is H; Y is Br, Cl, or I; $R^1$, $R^3$, and $R^4$ are independently the same or different and are H, linear or branched alkyl, linear or branched alkylaryl, hydroxyalkyl, or aryl; R is H, alkyl, aryl, alkylaryl, or hydroxyalkyl;

(c) treating the compound formed in step (b) with alkyl- or arylallyltrialkylstannane and a catalyst comprising palladium(O) under suitable conditions to form a compound having the structure:

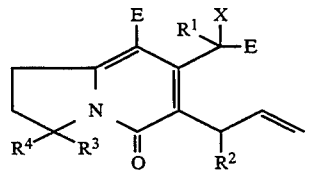

wherein E is CO,R, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; $R^2$ is alkyl or aryl; R is H, alkyl, aryl, alkylaryl, or hydroxyalkyl;

(d) reacting the compound formed in step (c) with alkali metal periodate or ozone and a reducing agent comprising alkali metal borohydride, wherein the alkali metal is either lithium, sodium, or potassium, under suitable conditions to form a compound having the structure:

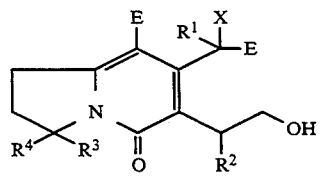

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; $R^2$ is alkyl or aryl; R is H, alkyl, aryl, alkylaryl, or hydroxyalkyl;

(e) lactonizing the compound formed in step (d) with a condensing reagent, comprising potassium trimethylsilyloxide followed by a dehydrating agent comprising N,N-dicyclohexylcarbodiimide and N,N-dimethylaminopyridine, under suitable conditions to form a compound having the structure:

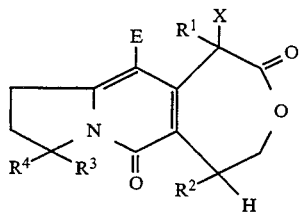

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; $R^2$ is alkyl or aryl; R is H, alkyl, aryl, alkylaryl, or hydroxyalkyl;

(f) hydroxylating the compound formed in step (e) with an hydroxylating reagent comprising the oxaziridine having the structure:

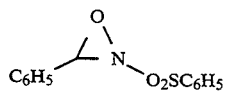

under suitable conditions to form a compound having the structure:

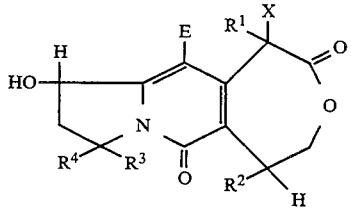

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; $R^2$ is alkyl or aryl; R is H, alkyl, aryl, alkylaryl, or hydroxyalkyl;

(g) oxidizing the compound formed in step (f) with an oxidant under suitable conditions to form a compound having the structure:

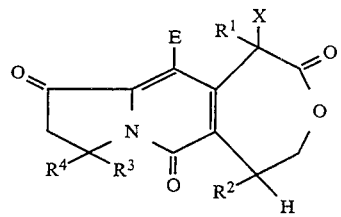

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; $R^2$ is alkyl or aryl; R is H, alkyl, aryl, alkylaryl, or hydroxyalkyl;

(h) condensing the compound formed in step (g) under suitable conditions to form a compound having the structure:

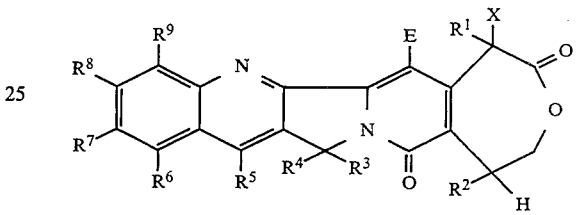

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl, or aryl; $R^2$ is alkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl;

(i) hydroxylating the compound formed in step (h) with a hydroxylating reagent under suitable conditions to form a compound having the structure:

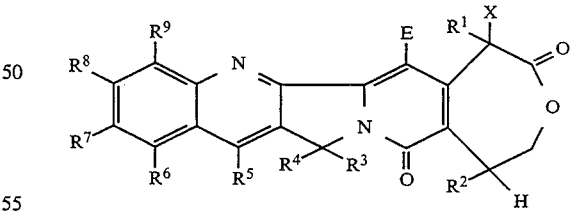

wherein E is $CO_2R$, $CONH_2$, CONHR, $CONR_2$, acyl, or CN; X is OH; $R^1$, $R^3$, and $R^4$ are independently the same or different and are H, linear or branched alkyl, linear or branched alkylaryl, hydroxyalkyl, or aryl; $R^2$ is alkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl. The oxidant of the oxidizing step (g) is favorably pyridinium dichromate. The hydroxylating reagent of step (j) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention further provides a process of synthesizing a compound having the structure:

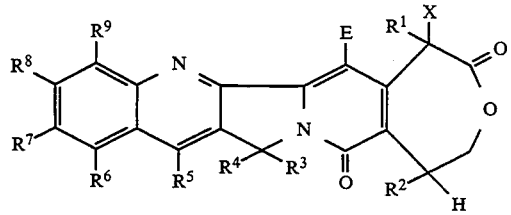

wherein E is H; X is OH; $R^1$, $R^3$, and $R^4$ are independently the same or different and are H, linear or branched alkyl, linear or branched alkylaryl, hydroxyalkyl, or aryl; $R^2$ is alkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, , alkyl aryl alkylaryl, or hydroxyalkyl; $R^{10}$, $R^{11}$ and $R^{12}$ are independently the same or different and are H, alkyl, aryl, alkylaryl, or acyl; which comprises:

(a) preparing a compound having the structure:

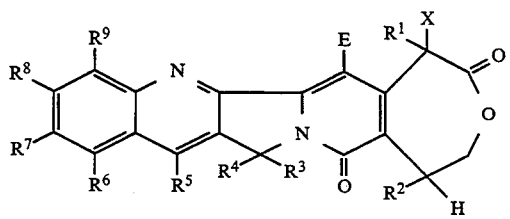

wherein E is $CO_2R$, $CONH_2$, CONHR, $CONR_2$, acyl, or CN; X is H; $R^1$, $R^3$, and $R^4$ are independently the same or different and are H, linear or branched alkyl, linear or branched alkylaryl, hydroxyalkyl or aryl; $R^2$ is alkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl alkylaryl, or hydroxyalkyl; $R^{10}$, $R^{11}$ and $R^{12}$ are independently the same or different and are H, alkyl, aryl, alkylaryl, or acyl; as described above;

(b) hydrolyzing and decarboxylating the compound formed in step (a) with an acid comprising aqueous hydrobromic acid under suitable conditions to form a compound having the structure:

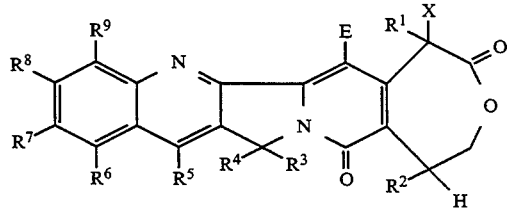

wherein E is H; X is H; $R^1$, $R^3$, and $R^4$ are independently the same or different and are H, linear or branched alkyl, linear or branched alkylaryl, hydroxyalkyl, or aryl; $R^2$ is alkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; and, (c) hydroxylating the compound formed in step (b) with a hydroxylating reagent under suitable conditions to form a compound having the structure:

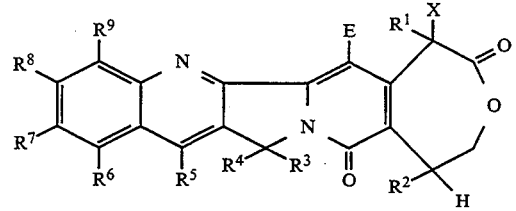

wherein E is H; X is OH; $R^1$, $R^3$, and $R^4$ are independently the same or different and are H, linear or branched alkyl, linear or branched alkylaryl, hydroxyalkyl, or aryl; $R^2$ is alkyl or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl. The hydroxylating reagent of step (c) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention provides a process of synthesizing a compound having the structure:

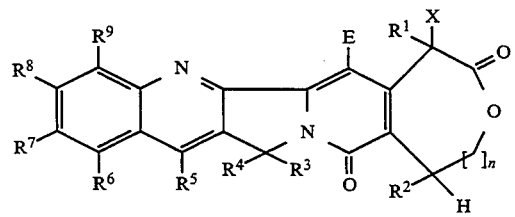

wherein E is H, $CO_2R$, $CONH_2$, CONHR, $CONR_2$, acyl, or CN; X, $R^1$ is O; $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; n is 0 or 1; which comprises:

(a) preparing a compound having the structure:

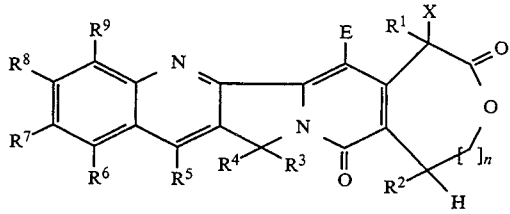

wherein $R^1$ is H; E is H, $CO_2R$, $CONH_2$, CONHR, $CONR_2$, acyl, or CN; X is H; $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; n is 0 or 1; as described above;

(b) hydroxylating the compound formed in step (a) with a hydroxylating reagent under suitable conditions to form a compound having the structure:

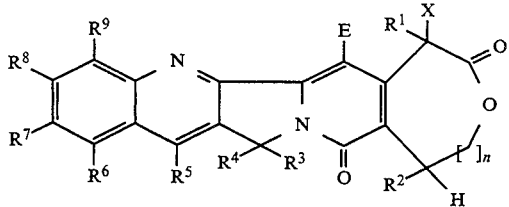

wherein E is H, $CO_2R$, $CONH_2$, CONHR, $CONR_2$, acyl, or CN; X is OH; $R^1$ is H; $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; n is 0 or 1; and, (c) oxidizing the compound formed in step (b) with an oxidant under suitable conditions to form a compound having the structure:

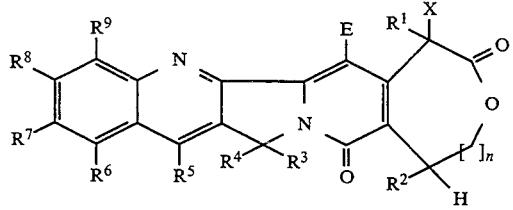

wherein E is H, $CO_2R$, $CONH_2$, CONHR, $CONR_2$, acyl, or CN; X, $R^1$ is O; $R^2$, $R^3$, and $R^4$ are independently the same or different and are H, linear or branched alkyl, linear or branched alkylaryl, hydroxyalkyl, or aryl; $R^5$, $R^6$, $R^7$, $R^8$, and $R^9$ are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; and, n is 0 or 1. The hydroxylating reagent of step (b) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention also encompasses a process of synthesizing enantiomerically pure compounds related to camptothecin and analogues thereof, wherein the configuration is exclusively R or S. The process comprises performing the hydroxylating step with the hydroxylating reagent having the structure:

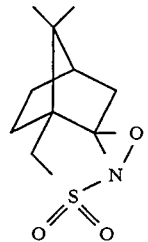

or the hydroxylating reagent of opposite configuration, respectively. While the value of the racemic mixture of camptothecins provided by non-enantiospecific routes is considerable, given the high native biological activity of camptothecin, the possibility of obtaining still higher activities in an optically pure analogue suggest the clinical importance of the present invention.

The invention also includes a process of synthesizing a compound having the structure:

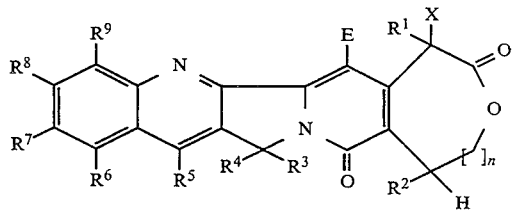

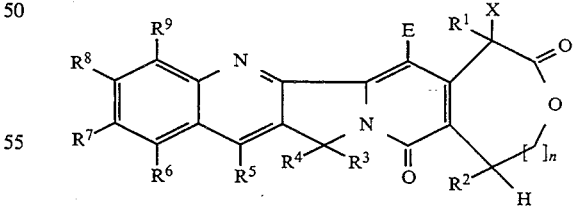

wherein E is H, $CO_2R$, $CONH_2$, CONMR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$, and $R^9$ are C-glycal, and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl aryl alkylaryl, or hydroxyalkyl; $R^{10}$, $R^{11}$ and $R^{12}$ are independently the same or different and are H, alkyl, aryl, alkylaryl, or acyl; and, n is 0 or 1; which comprises:

(a) preparing a compound having the structure:

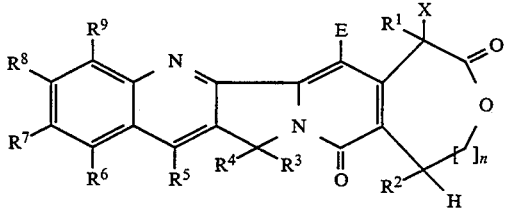

wherein E is H, $CO_2R$, $CONH_2$, CONHR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$ and $R^9$ are $OR^{13}$, and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $Sr^{10}$, or $NR^{11}R^{12}$; R is H, alkyl aryl alkylaryl, or hydroxyalkyl; $R^{10}$, $R^{11}$ and $R^{12}$ are independently the same or different and are H, alkyl, aryl, alkylaryl, or acyl; $R^{13}$ is H; and, n is 0 or 1; as described above;

(b) reacting the compound formed in step (a) with a reagent comprising $PhN(CF_3SO_2)_2$ under suitable conditions to form a triflate compound having the structure:

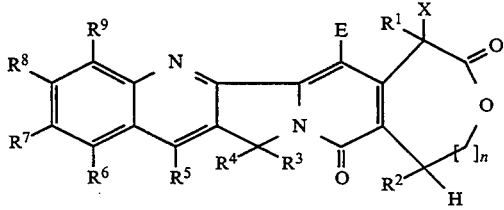

wherein E is H, $CO_2R$, $CONH_2$, CONHR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$ and $R^9$ are $OR^{13}$, and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; $R^{13}$ is $SO_2CF_3$; n is 0 or 1; and, (c) coupling the compound formed in reacting step (b) with a stannylated glycal under suitable conditions to form the compound having the structure:

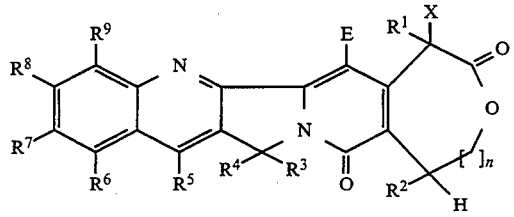

wherein E is H, $CO_2R$, $CONH_2$, CONHR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$, and $R^9$ are C-glycol, and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; and, n is 0 or 1.

The invention also provides a process of synthesizing a compound having the structure:

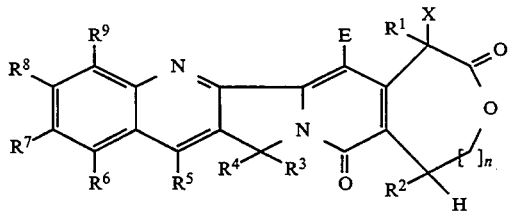

wherein E is H, $CO_2R$, $CONH_2$, CONHR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$, and $R^9$ are $OR^{13}$, and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, or $SR^{10}$, $NR^{11}R^{12}$; R is H, alkyl aryl alkylaryl, or hydroxyalkyl; $R^{10}$, $R^{11}$ and $R^{12}$ are independently the same or different and are H, alkyl, aryl, alkylaryl, or acyl; $R^{13}$ is a 0-glycosyl; and, n is 0 or 1; which comprises:

(a) preparing a compound having the structure:

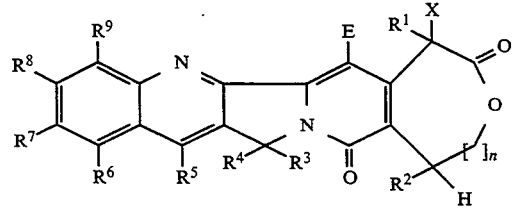

wherein E is H, $CO_2R$, $CONH_2$, CONHR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$, and $R^9$ are $OR^{13}$, and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, or $NR^{11}R^{12}$; R is H, alkyl, aryl, alkylaryl, or hydroxyalkyl; $R^{10}$, $R^{11}$ and $R^{12}$ are independently the same or different and are H, alkyl, aryl, alkylaryl, or acyl; $R^{13}$ is H; and, n is 0 or 1; as described above; and, (b) reacting the compound formed in step (a) with a reagent comprising a glycosyl epoxide under suitable conditions to form a compound having the structure:

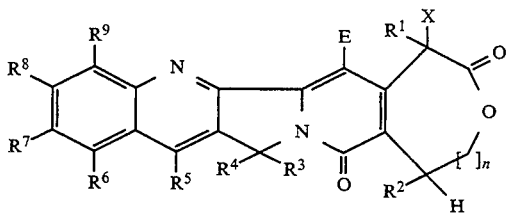

wherein E is H, $CO_2R$, $CONH_2$, CONHR, $CONR_2$, acyl, or CN; X, $R^1$ is O, or X is H or OH and $R^1$ is H, linear or branched alkyl, linear or branched alkylaryl, hydroxyalkyl, or aryl; $R^2$, $R^3$, and $R^4$ are independently the same or different and are H, linear or branched alkyl, linear or branched alkylaryl, hydroxyalkyl, or aryl; one or more of the group $R^5$, $R^6$, $R^7$, $R^8$ and $R^9$ are $OR^{13}$ and the others are independently the same or different and are H, linear or branched alkyl, linear or branched alkylaryl, aryl, $CO_2R$, alkoxy, aryloxy, hydroxyalkyl, nitro, cyano, aminoalkoxy, Cl, F, Br, I, $SR^{10}$, $NR^{11}R^{12}$; R is H, alkyl aryl alkylaryl, or hydroxyalkyl; $R^{10}$ $R^{11}$ and $R^{12}$ are independently the same or different and are H, alkyl, aryl, alkylaryl, or acyl; $R^{13}$ is O-glycosyl; and, n is 0 or 1.

Biological Properties

Cytotoxicity Assay. The synthesized compounds were evaluated for their cytotoxic effects on HL-60 (human promyelocytic leukemia) cells. The assay was conducted in 96-well microplates. The compounds were serially diluted in 4 to 6 steps with dimethylsulfoxide and added to cell incubation medium (RPMI 1640 containing 10% fetal cell serum) at the final concentration of 1.0% dimethylsulfoxide in the medium. The cytotoxicity of the compounds were determined by the XTT-microculture tetrazolium assay: 2′,3′-bis(2-methoxy-4-nitro-5-sulfophenyl)-3-[(phenylamino)carbonyl]-2H-tetrazolium hydroxide (XTT) was prepared at 1 mg/mL in prewarmed (37° C.) medium without serum. Phenazine methosulfate (PMS) and fresh XTT were mixed together to obtain 0.075 mM PMS-XTT solution (25 mL of the stock with 5mg PMS added per 5 mL of 1 mg/mL XTT). Fifty microliters of this mixture were added to each well of the cell culture after 72 hours exposure to the testing compound. After incubation at 37° C. for 6 hours, the absorbance was determined at 450 nm and 630nm with a microplate reader (EL 340, Bio-Tek Instruments, Inc., Winooski, Vt.). The median-effect inhibitory concentration ($IC_{50}$) was determined from a medium-effect plot using computer software for the purpose.

The results of the assay of cytotoxicity towards HL-60 cells of several analogues of camptothecin provided by the invention are illustrated in the accompanying Table I, along with comparison data for native camptothecin. The data shown indicate that the new camptothecin analogues have significant cytotoxic activity against cancer cells.

The present invention therefore provides a method of treating cancer, which comprises administering an anti-cancer-effective quantity of any of the analogues of camptothecin disclosed herein. The drug may be administered to a patient afflicted with cancer by any conventional route of administration, including, but not limited to, intravenous, intramuscular, oral, subcutaneous, intratumoral, intradermal, and parenteral. The anticancer-effective quantity is between 0.01 mg and 10.0 mg per kg of subject body weight.

The present invention also provides a pharmaceutical composition comprising any of the analogues of camptothecin disclosed herein and a pharmaceutically acceptable carrier. The composition may contain between 1 mg and 500 mg of a camptothecin analogue, and may be constituted into any form suitable for the mode of administration selected. Compositions suitable for oral administration include solid forms, Such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

Optimal dosages to be administered may be determined by those skilled in the art, and will vary with the particular camptothecin analogue in use, the strength of the preparation, the mode of administration, and the advancement of the disease condition. Additional factors depending on the particular patient being treated will result in a need to adjust dosages, including patient age, weight, gender, diet, and time of administration.

TABLE I

| Cytotoxicity of Camptothecin and Analogues on HI-60 cell growth during 72 hr exposure[a] (XTT assay) | | | |
|---|---|---|---|
| | Inhibitory Concentrations (μM) | | |
| Compound | $IC_{50}$ | $IC_{70}$ | $IC_{95}$ |
| Camptothecin | 0.0094 | 0.012 | 0.25 |
| 20-Deoxycamptothecin | 0.039 | 0.052 | 0.109 |
| 14-Carbomethoxy-deoxycamptothecin | 0.194 | 0.318 | 1.082 |
| 14-Carbohydroxy deoxycamptothecin | 2.44 | 12.0 | 618.7 |
| 14-Carbomethoxy Camptothecin | >5 | N.D.[b] | N.D. |
| 17-Methyl Camptothecin | 0.266 | 0.432 | 1.432 |

[a]All compounds were dissolved in DMSO and heated at 50° C. prior to serial dilution with DMSO.
[b]Not determined.

The following Experimental Details are set forth to aid in an understanding of the invention, and are not intended, and should not be construed, to limit in any way the invention set forth in the claims which follow thereafter.

EXPERIMENTAL DETAILS

General

All air and moisture sensitive reactions were performed in a flame-dried apparatus under a nitrogen atmosphere unless otherwise noted. Air-sensitive liquids and solutions were transferred via syringe or cannula. Unless otherwise noted, all solvents and reagents were commercial grade and were used as sold. The following are exceptions, and are all distilled under nitrogen using the drying methods listed in parentheses: dichloromethane (calcium hydride), benzene (calcium hydride), tetrahydrofuran (sodium/benzophenone ketyl), diethyl ether (sodium/benzophenone ketyl), diisopropylamine (calcium hydride).

Melting points (mp) were uncorrected and performed in soft glass capillary tubes using an Electrothermal series IA9100 digital melting point apparatus. Infrared (IR) spectra were obtained with a Perkin-Elmer 1600 Series Fourier Transform Spectrometer. Samples were prepared as neat films on NaCl plates unless otherwise noted. Proton nuclear magnetic resonance (1H NMR) spectra were determined using a Bruker AMX-400 spectrometer operating at 400 MHz. Carbon nuclear magnetic resonance (13C NMR) spectra were obtained on a Bruker AMX-400 spectrometer operating at 100 MHz with composite pulse decoupling.

High resolution mass spectra (HRMS) were determined by electron impact ionization (EI) on a JEOL JMS-DX 303HF mass spectrometer with perfluorokerosene (PFK) as an internal standard.

Flash chromatography was carried out on silica gel according to the protocol of Still (W. C. Still, et al., *J. Org. Chem.*, 43, 2923 (1978)).

EXAMPLE 1

Preparation of 2-Methoxypyrroline

To the stirring neat dimethyl sulfate (265.0 g, 2.1 mol) was added dropwise 2-pyrrolidinone (170 g, 2.00 mol) over 2 h. The reaction was then heated at 60C for 16 h. After cooling the reaction to room temperature, it was poured onto ice (500 g) mixed with potassium carbonate (300 g). The organic layer was separated and the aqueous layer was extracted with ether (3×100 mL). The combined organic layer and extracts were dried over anhydrous magnesium sulfate, filtered, and concentrated under vacuum (the bath temperature was kept under 20° C.). The resulting solution was distilled under vacuum to give 156.4 g (37°–40° C., 74 torr), which was redistilled at 115°–120° C. under atmosphere to give of the desired product (129 g, 65%).

$^1$H NMR (400 MHz, CDCl3) 3.80 (s, 3 H),3.65(tt, J =1.2, 7.1 Hz, 2H), 2.43 (tt, J =1.2, 7.4 Hz, 2H), 2.02 (m, 2H).

$^{13}$C NMR (100 MHz, CDCl3) 10.10 (brs, 1H), 3.73 (t, J =7.6 Hz, 2 H),3.39 (t, J =8.0 Hz, 2 H) , 2.16 (quintet, J=7.7 Hz, 2H) , 1.68 ( s, 6H).

EXAMPLE 2

Isopropylidene α-(Tetrahydro-2-pyrrolidene)malonate (3)

A solution of 2 (55.8 g, 0.563 mol), Meldrum's acid (81.1 g, 0.563 mol) and triethylamine (10 mL) in benzene (300 mL) was refluxed 10 h. The solid residue after evaporation of the reaction mixture was recrystallized from absolute ethanol to give the desired product 3 as white crystals (110.0 g, 92.5%).

$^1$H NMR (400 MHz, CDCl3) δ 10.10 (brs, 1H), 3.73 (t, J =7.6 Hz, 2H), 3.39 (t, J =8.0 Hz, 2H), 2.16 (quintet, J =7.7 Hz, 2H), 1.68 (s, 6H).

EXAMPLE 3

2-carbomethoxymethylenepyrroline (4)

To the solution of 3 (42.2 g, 200 mmol) in anhydrous methanol (200 mL) was added a solution of sodium methoxide in methanol (25% w/w, 47.5 g, 220 mmol), and the resulting solution was refluxed 2 h. The reaction mixture was concentrated under vacuum to a semi solid before iced water (200 mL) was added to it. The resulting solution was adjusted to pH 5–6 by 2N HCl, and extracted with methylene chloride (5×100 mL). The combined extracts was dried over anyhydrous magnesium sulfate, filtered, and concentrated to give yellow solid. Recrystallization of the residue solid from hexane afforded the desired product as pale yellow solid (27.6 g, 97.7%).

$^1$H NMR (400 MHz, CDCl3) 7.88 (brs, 1 H) ,4.53(s, 1H), 3.62 (s,3H0, 3.51 (t,J=6.9 Hz, 2H), 2.57 (t,J=7.7 Hz, 2 H), 1.96 (quintet, J=Hz, 2H).

$^{13}$C NMR (100 MHz, CDCl3) 171.0, 166.6, 76.2, 50.0, 47.0, 32.2, 22.0 ppm.

IR (neat) 3365, 2948, 2881, 1652, 1603, 1501, 1237, 1146, 1064, 777cm$^{-1}$.

EXAMPLE 4

3-Carbomethoxymethyl-4-carbomethoxy-1,6-cyclopentano-2-pyridone (6)

To the solution of 4 (27.6 g, 195 mmol) in absolute ethanol (200 mL) was added dimethyl 1,3-allenyldicarboxylate 514 (33.6 g, 215 mmol) and triethylamine (2 mL). The reaction was stirred at room temperature for 65 h. The reaction mixture was concentrated to near dryness. Trituration of the residue with dry ether (50 mL) afforded 6 as a white solid (47.8 g, 92.3%).

$^1$H NMR (400 MHz, CDCl3) δ 6.21 (s, 1H), 4.11 (t, J =7.4 Hz, 2H), 3.74 (s, 3H), 3.73 (s, 2H), 3.66 (s, 3H), 3.44 (t, J=7.9 Hz, 2H), 2.16 (quintet, J=7.6 Hz, 2H).

$^{13}$C NMR (100 MHz, CDCl3) δ 170.9, 165.8, 161.0, 157.4, 147.1, 120.1, 166.5, 52.1, 51.6, 49.1, 41.1, 34.7, 20.6 ppm. IR (neat) 2953, 1734, 1716, 1656,1520, 1436, 1294, 1203 cm$^{-1}$.

EXAMPLE 5

3-(1-Carbomethoxypropyl)-4-carbomethoxy-1,6-cyclopentano-2-pyrridone (7)

To a solution of pyridone 6 (47.0 g, 177 mmol) in anhydrous dimethoxyethane (700 mL) at −78° C. was added potassium t-butoxide (20.8 g, 186 mmol). After 20 min ethyl iodide (50.3 g, 354 retool) was added and the solution was allowed to warm to room temperature and stirred for 30 h. The reaction mixture was then poured to brine (300 mL) and the aqueous layer extracted with methylene chloride (4×200 mL). The combined organic phase and the extracts was dried over anhydrous magnesium sulfate, filtered, and concentrated. The semi-solid residue was then recrystallized from ethyl acetate to give 7 as a pale yellowish green solid (36.54 g, 2 crops). The mother liquid was subjected to flash chromatography with ethyl acetate to afford more product 7 (11.2 g, total yield 91.0%).

¹H NMR (400 MHz, CDCl₃ δ 6.35 (s, 1H), 4.13 (dt, J=1.2, 7.5 Hz, 2H), 3.99 (t, J=7.2 Hz, 1H), 3.80 (s, 3H), 3.64 (s, 3H), 3.39 (dt, J=2.6, 8.0 Hz, 2H), 2.17 (quintet, J=7.6 Hz, 2H), 2.05 (m, 1H), 0.91 (t, J=7.4 Hz, 3H).

¹³C NMR (100 MHz, CDCl₃δ 173.0, 166.1, 161.1, 156.3, 151.6, 117.2, 107.0, 53.1, 51.7, 49.8, 49.2, 34.5, 25.4, 20.7, 12.4 ppm.

IR (neat) 2959, 2919, 1714, 1710, 1668, 1585, 1516, 1437, 1352, 1273, 1193, 1094, 1032, 976.3 cm⁻¹.

EXAMPLE 6

4-Carbomethoxy-de-AB-deoxycamptothecin (8)

A mixture of 7 (5.01 g, 17.1 mmol), formaldehyde (3.08 g), concentrated sulfuric acid (1 mL) and water (1 mL) in dioxane (25 mL) and extracted with methylene chloride (4×50 mL). The combined extracts was dried over anhydrous magnesium sulfate, filtered, and concentrated to a pale yellow sticky oil 8 which was already pure as shown by 1H NMR. The product was used directly for the next step.

¹HNMR (400MHz, CDCl₃) δ 5.48 (d, J=5.8 Hz, 1H), 5.13 (d, J=5.8 Hz, 1H), 4.34 (dd, J=5.1, 9.1 Hz, 1H), 4.19, (dt, J=2.9, 7.6 Hz, 2H), 3.85, (s, 3H), 3.48 (dt, J=3.6, 7.9 Hz, 2H), 2.22 (quintet, J=7.6 Hz, 2H), 1.65-2.01 (m, 2H), 1.08 (t, J=7.6 Hz, 3H).

¹³C NMR (100 MHz, CDCl₃) 6 171.3, 165.2, 157.9, 167.0, 147.3, 118.5, 104.9, 65.0, 52.0, 49.5, 44.3, 34.8, 25.3, 20.7, 11.9 ppm.

IR (neat) 2925, 1734, 1713, 1650, 1548, 1440, 1309, 1170, 1097, 1047 cm⁻¹.

EXAMPLE 7

De-AB-deoxycampothecin (9)

A mixture of 8 in aqueous hydrobromic acid (48%, 50 mL) was heated at 105° C. for 18 h. It was then poured into brine (60 mL) and extracted with methylene chloride (4×50 mL). The combined extracts was dried over anhydrous magnesium sulfate, filtered, and concentrated. The residue was then subjected to flash chromatography with 50:50:1 chloroform/ethyl acetate/methanol to afford 9 as an off-white solid (2.11 g, 52.9%).

¹H NMR (400 MHz, CDCl₃) δ 5.98 (s, 1H), 5.38 (d, J=5.7 Hz, 1H), 5.20 (d, J=5.7 Hz, 1H), 4.12 (t, J=7.3 Hz, 2H), 3.35 (t, J=6.6 HZ, 1H), 3.08 (t, J=7.7 Hz, 2H), 2.21 (quintet, J=7.74 Hz, 2H), 1.80-1.98 (m, 2H), 0.99 (t, J=7.4 Hz, 3H).

¹³C NMR (100 MHz, CDCl₃) δ 171.4, 158.5, 150.5, 146.6, 117.2, 100.2, 66.1, 48.6, 45.8, 31.8, 25.1, 21.5, 11.3 ppm.

EXAMPLE 8

7-Hydroxy-AB-campothecin (10)

A mixture of 9 (778 mg, 3.33 mmol), selenium dioxide (1.85 g, 16.7 mmol) in wet dioxane (95%, 20 mL) in a sealed tube was heated at 155° C. for 4h. It was then poured into water and extracted with methylene chloride (4×30 mL). The combined extracts was dried over anhydrous magnesium sulfate, filtered, and concentrated. The dark solid residue was then chromatographed with 25% acetone in chloroform (300 mL) and 30: 20: 1 chloroform/acetone/methanol (500 mL) to afford 10 as a yellowish solid (377.4 mg, 42.7%). The diastereomeric ratio is about 1:1.

¹H NMR (400 MHz, DMSO-d₆ with 1 small drop of D₂O) δ 6.51 (s, 1H), 5.25 (dd, J=15.4, 19.0 Hz, 2H), 5.13 (t, J=7.0 Hz, 1H), 4.08 9, 1H), 2.42 (m, 1H), 1.93 (m, 1H), 1.76 (m, 2H), 0.82 (t, J=7.1 Hz, 3H).

¹³C NMR (100 MHz, DMSO-d₆) δ 172.59, 172.54, 156.87, 152.94, 152.90, 149.83, 149.78, 116.33, 97.37, 72.09, 72.04, 71.94, 65.16, 59.68, 45.62, 31.25, 31.19, 30.30, 30.26, 7.66 ppm (21 peaks observed).

HRMS calculated for C₁₃H₁₅NO₅ (M+) 265. 0950, observed 265.0952.

EXAMPLE 9

7-Oxo-de-AB-camptothecin (11)

To the suspension of 10 (356.1 mg, 1.34 mmol) and 4 Å molecular sieves (activated powder, 1.50 g) in methylene chloride (15 mL) at 0° C. was added pyridinium dichoromate (1.01 g. 2.68 mmol). After 3.5 h, 30 mL ethyl acetate was added to the mixture, and it was filtered through a plug of silica gel and celite. The residue after evaporation of the filtrate was flash chromatographed with 1:1 chloroform/ethyl acetate to give 11 (159.6 rag, 45.2%).

¹H NMR (400 MHz, CDCl₃) 6 7.23, (s, 1H), 5.68, (d, J=7.1 Hz, 1 H), 5.25, (d, J=7.1 Hz, 1H), 4.35 (t, J=6.8 Hz, 2H), 3.65 (s, 1H, from the OH), 2.97 (t, J=6.8 Hz, 2H), 1.82 (m, 2H), 0.99 (t, J=7.4 Hz, 3H).

¹³C NMR (100 MHz, CDCl₃) δ 196.0, 173.3, 157.7, 149.3, 139.9, 124.5, 100.8, 72.3, 66.3, 42.2, 33.7, 31.8, 7.7 ppm.

HRMS calculated for C₁₃H₁₃NO₅ (M+) 263. 0794, observed 263.0809.

EXAMPLE 10 dl-Camptothecin (1)

A suspension of 11 (185.2 mg, 0.704 mmol) and 12 (178 mg, 0.844 mmol; W. Borsche, et al., *Chem. Ber.*, 76, 1099 (1943)) in toluene (20 mL) was refluxed for 0.5h . Then, toluenesulfonic acid monohydride (10 mg) was added, and the reaction was refluxed with a Dean-Starr trap for 3.5 h. The reaction was cooled to room temperature and most solvent was evaporated in vacuum. The residue was flash chromatographed with 100: 10:1 chloroform/acetonitrile/methanol to give 196.5 mg (80.3%) brown-yellow solid. Recrystallization with 10% methanol in chloroform gave 173.1 mg off-white solid, m.p. 264°-265° C. (dec).

¹H NMR (400 MHz, DMSOOd₆) δ 8.70 (s, 1 H), 8.16 (m, 2H), 7.88 (t, J=7.5 Hz, 1H), 7.72 (t, J-Hz, 1H), 7.36 (s, 1H), 6.54 (s, 1H), 5.43 (s, 2H), 5.30, (s, 1H), 1.87 (m, 2H), 0.88 (t, J=7.0 Hz).

¹³C NMR (100 MHz, CDCl₃) δ 172.4, 156.8, 149.9, 147.9, 145.4, 131.6, 130.3, 129.8, 129.0, 128.4, 127.9, 127.6, 119.0, 96.6, 72.3, 65.2, 50.2, 30.2, 7.7 ppm (19 peaks observed). HRMS (FAB) calculated for C₂₀H₁₆N₂O₄ (M+1)+ 349.1188, observed 349.1184.

EXAMPLE 11

4-Carbomethoxy-7-hydroxy-de-AB-deoxycampothecin (14)

To a solution of 8 (1.20 g, 4.12 mmol) in THF (20 mL) at −78° C. was added KHMDS (1.9 g, 9.06 retool) in THF (10 mL) and Davis' oxazirdine (1.05 g, 4.04 mmol) in THF (10 mL) simultaneously over 20 min. A solution of saturated ammonium chloride (10 mL) was added to the reaction mixture in 10 min, and the reaction was left to warm up to room temperature. The reaction mixture was poured into a brine solution, and the aqueous phase was extracted with chloroform (30 mL×3). The combined organic phase and the extracts were dried over anhydrous magnesium sulfate, filtered, and concentrated. The residue was then loaded onto a flash column, eluted with 30% ethyl acetate in chloroform (500 mL) and 15% acetone in chloroform (1500 mL) to give 15 (246 mg, 19%) and the desired secondary alcohol 14 (707 mg, 56%) as a mixture of diastereomers (1.3:1 ratio from integration of $^1$HNMR.)

$^1$H NMR (400 MHz, CDCl$_3$) δ 5.40–5.52 (m, 3H), 5.10 (m, 2H), 4.42 & 4.05 (1H), 4.24 (m, 2H), 3.90 (s, 3H), 2.31 (m, 2H), 1.70–1.91 (m, 2H), 1.09 & 0.98 (2t's, J=7.3 Hz, 3H).

IR (neat) 3390, 2958, 1732, 1651, 1556, 1435, 1306, 1157, 1090, 748 cm$^{-1}$.

EXAMPLE 12

4-Carbomethoxy-7-oxo-de-AB-deoxycampothecin (16)

A mixture of 14 (595 mg, 1.94 mmol), PDC (2.18 g, 5.80 mmol) and activated 4 A molecular sieve powder (2.20 g) in methylene chloride (20 mL) was stirred at 0°–5° C. for 4 h. It was then diluted with ethyl acetate (30 mL) and filtered through celite. The flask and the residue was rinsed and washed with 50% ethyl acetate in chloroform (20 mL×5) and the filtrate was concentrated in vacuum to give pure 16 (490.2 mg, 83%).

$^1$H NMR (400 MHz, CDCl$_3$) δ 5.55 (d, J=17.2 Hz, 1H), 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m, 1H), 1.04 (t, J=7.4 Hz, 3H).

$^{13}$C NMR (100 MHz, CDCl$_3$) δ 194.3, 169.5, 164.0, 157.2, 144.6, 137.7, 126.4, 110.2, 65.7, 53.4, 43.6, 42.2, 33.7, 26.1, 11.5 ppm.

IR (neat) 2952, 1742, 1658, 1614, 1440, 1300, 1159, 1057 cm$^{-1}$.

EXAMPLE 13

A solution of 16 (601 mg, 0.197 mmol) and 12 (497 mg, 2.36 mmol) in toluene (20 mL) was refluxed for 40 min. Then toluenesulfonic acid monohydrate (20 mg) was added, and the reaction flask was equipped with a Dean-Stark trap. Reflux was continued for 4 h before the reaction was cooled to room temperature. It was concentrated to about 10 mL via vacuum, and filtered. The solid thus obtained was recrystallized from chloroform to give 17 (578 mg 75%), m.p. 300°–302° C.(dec).

$^1$H NMR (400 MHz, CDCl$_3$) δ 8.38 (s, 1H), 8.11 (d, J=8.4 Hz, 1H), 7.91 (d, J=8.2 Hz, 1H), 7.81 (dt, J=1.2, 7.7 Hz, 1H), 7.66 (t, J=7.5 Hz, 1H), 5.62 (d, J=16.2 Hz, 5.30 (d, J=16.2 Hz, 1H), 5.28 (s, 2H), 4.12 (s, 3H), 3.78 (dd, J=5.2, 8.7 Hz, 1H), 2.12 (m, 1H), 1.93 (m, 1H), 1.11 (t, J=7.4 Hz, 3H).

$^{13}$C NMR (100 MHz, CDCl$_3$) δ 170.2, 165.6, 157.2, 151.4, 148.8, 145.1, 144.4, 130.9, 130.6, 130.3, 128.53, 128.48, 128.04, 127.99, 120.5, 108.3, 65.7, 52.9, 50.2, 44.1, 26.0, 11.6 ppm. HRMS calculated for C$_{22}$H$_{18}$N$_2$O$_5$ (M+) 390.1216, observed 390.1231.

EXAMPLE 14

Deoxycampothecin (18)

A solution of 17 (207.5 mg, 0.531 mmol) in 48% aqueous hydrobromic acid (8 mL) in a sealed tube was heated for 15 h at 140° C. After it was cooled, the reaction mixture was concentrated to near dryness via vacuum. The mixture was then carefully neutralized with sodium hydroxide; 2 N) and saturated sodium bicarbonate to pH 6–8. The aqueous mixture was extracted with chloroform (15 mL×10). The combined extracts were dried over anhydrous magnesium sulfate, filtered, and concentrated. The residue was flash chromotographed with 2% methanol in chloroform to give 18 (124.3 rag, 71%).

HRMS calculated for C$_{20}$H$_{16}$N$_2$O$_3$ (M+) 332. 1161, observed 332.1151.

EXAMPLE 15 dl-Camptothecin (1)

To a solution of 18 (47.8 rag, 0. 144 retool), copper (II) chloride (80 mg) and dimethylamine (100 µl) in DMF (16 mL) was bubbled in oxygen for 7 h. The reaction mixture was concentrated in vacuum to about 5 mL, and was then diluted with water. A solution of saturated ammonium chloride was used to adjusted the pH of the above mixture to about 6, and the resulting mixture was extracted with chloroform (10 mL ×10). The combined extracts were dried over anhydrous magnesium sulfate, filtered, and concentrated. The residue was flash chromatographed with 2% methanol in chloroform to give dl-camptothecin (45.5 mg, 91%).

What is claimed is:

1. A compound having the structure:

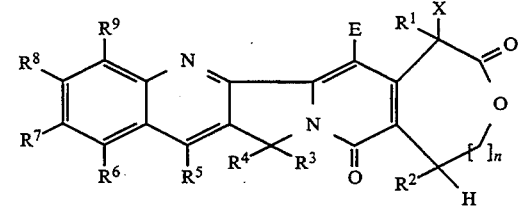

wherein E is H, CO$_2$R, CONH$_2$, CONHR, CONR$_2$ or CN; (a) X and R$^1$ together are 0, or (b) X is H or OH, and R$^1$ is H, linear or branched alkyl, linear or branched alkylaryl, hydroxyalkyl or aryl; R$^2$, R$^3$, and R$^4$ are independently the same or different and are H, linear or branched alkyl, linear or branched alkylaryl, hydroxyalkyl or aryl; R$^5$, R$^6$, R$^7$, R$^8$ and R$^9$ are independently the same or different and are H, linear or branched alkyl, linear or branched alkylaryl, aryl, CO$_2$R, alkoxy, aryloxy, hydroxyalkyl, C-glycal, nitro, cyano, aminoalkoxy, Cl, F, Br, I, SR$^{10}$ or NR$^{11}$R$^{12}$, provided that at least one of R$^5$, R$^6$, R$^7$, R$^8$, and R$^9$ is C-glycal; R is H, alkyl, aryl, alkylaryl or hydroxyalkyl; R$^{10}$, R$^{11}$ and R$^{12}$ are independently the same or different and are H, alkyl, aryl, alkylaryl or acyl; and n is 0 or 1.

2. The compound of claim 1, wherein E is H.
3. The compound of claim 2, wherein R$^1$ is ethyl.
4. The compound of claim 3, wherein X is OH.
5. The compound of claim 4, wherein R$^2$ is CH$_3$.
6. The compound of claim 5, wherein R$^3$, and R$^4$ are H.
7. The compound of claim 3, wherein X is H.
8. The compound of claim 7, wherein R$^2$ is CH$_3$.
9. The compound of claim 8, wherein R$^3$, and R$^4$ are H.
10. The compound of claim 1, wherein E is CO$_2$R, and R is selected from the group consisting of methyl, ethyl, propyl, butyl, benzyl, and phenyl.
11. The compound of claim 10, wherein R$^1$ is ethyl.
12. The compound of claim 11, wherein X is OH.
13. The compound of claim 12, wherein R$^2$ is CH$_3$.
14. The compound of claim 13, wherein R$^3$, and R$^4$ are H.

15. The compound of claim 10, wherein X is H.

16. The compound of claim 15, wherein $R^2$ is $CH_3$.

17. The compound of claim 15, wherein $R^3$, and $R^4$ are H.

18. A pharmaceutical composition which comprises an anticancer-effective amount of the compound of claim 1 and a pharmaceutically acceptable carrier.

19. The pharmaceutical composition of claim 1, wherein the anticancer-effective amount is between 1 mg and 500 mg.

20. A method of treating cancer which comprises administering to a subject an anticancer-effective amount of the compound of claim 1 and a pharmaceutically acceptable carrier.

21. The method of claim 18, wherein the anticancer-effective quantity is between 0.01 mg and 10.0 mg per kg of subject body weight.

* * * * *